US006284474B1

(12) United States Patent
Dobbs et al.

(10) Patent No.: US 6,284,474 B1
(45) Date of Patent: Sep. 4, 2001

(54) DETECTION AND DIAGNOSIS OF CONDITIONS ASSOCIATED WITH LUNG INJURY

(75) Inventors: Leland G. Dobbs, Oakland; Robert Gonzalez, San Francisco, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/065,647

(22) Filed: Apr. 23, 1998

(51) Int. Cl.$^7$ .................................................. G01N 33/567
(52) U.S. Cl. .................... 435/7.21; 435/7.7; 435/7.72; 435/7.92; 435/8; 530/388.85; 530/388.2; 530/389.1
(58) Field of Search ............................... 424/9.34, 178.1, 424/530, 545; 435/7.2, 2, 7.21, 7.1, 7.7, 7.72, 7.9, 7.92, 7.94, 7.93, 35; 530/391.1, 391.3, 413, 388.85, 388.2, 389.1; 436/518, 536, 811

(56) References Cited

PUBLICATIONS

Henry et al.; Clinical Diagnosis and Management by Laboratory Methods; p. 602, 1979.*
Rae et al. ; The Lancet; vol. 344; Nov. 26, 1994; p. 1472–73.*
Samuel et al.; J. of Bioluminsecence and Chemiluminescence; vol. 5; p. 179–182, 1990.*
Singh et al.; Microscopy Research and Technique; 26; 357–365, 1993.*
McElroy et al.; Prog. Respir. Res. 165–168, 1994.*
Singh et al., "The distribution and molecular presentation of the brush border antigen and Heymann nephritis in various rat tissues" *Clin. exp. Immunol.* (1985) 60:579–585.
Kotas et al., "Luminal Surfaces of Fetal Rat Alveolar Type II and Clara Lung Cells React with Antibody to Heymann Nephritis Antigen" *Pediatric Pulmonology* (1991) 10:260–266.
Sahali et al., "Comparative Immunochemistry and Ontogeny of Two Closely Related Coated Pit Proteins" *American Journal of Pathology* (1993) 142(5):1654–1667.
Makker et al., "Definition of an Immunologic Marker for Type II Pneumocytes" *Journal of Immunology* (1989) 142(7):2264–2269.
Funkhouser et al., "Monoclonal Antibody Isolation of Type II Pneumocytes" *Cytometry* (1987) 8(3):321–326.

Kasper et al., "Immunohistochemistry of new type I alveolar epithelial cell markers of the rat" *Histol Histopathol* (1996) 11:145–152.
Lwebuga–Mukasa, "Isolation and Partial Characterization of Pneumocin, a Novel Apical Membrane Surface Glycoprotein Marker of Rat Type II Cells" *Am. J. Respir. Cell Mol. Biol.* (1991) 4(6):479–488.
Lwebuga–Mukasa, "A $Mn^{2+}$–enhanced, RGD–dependent Adhesion Technique for Isolation of Adult Rat Type II Alveolar Epithelial Cells for Immediate Functional Studies" *Am. J. Respir. Cell Mol. Biol.* (1994) 10(4):347–354.
Williams et al., "Expression of Cell–specific Markers for Alveolar Epithelium in Fetal Rat Lung" *Am. J. Respir. Cell Mol. Biol.* (1990) 2(6):533–542.
Suehiro et al., "Immunohistochemical Study of Lung Adenocarcinoma Using Monoclonal Antibody for 60–Kilodalton Antigen in Type II Pneumocytes and Nonciliated Bronchiolar Epithelial Cells" *Am. J. Clin. Pathol.* (1989) 92(2):150–158.
Marshall et al., "Identification and characterization of the pulmonary alveolar type II cell" *Biochimica et Biophysica Acta* (1988) 966(3):403–413.
Funkhouser et al., "Monoclonal Antibody Identification of a Type II Alveolar Epithelial Cell Antigen and Expression of the Antigen during Lung Development" *Developmental Biology* (1987) 119:190–198.
Dobbs, "Isolation and culture of alveolar type II cells" *Am. J. Physiol.*(1990) 258(4 Pt 1):L134–L147.
Lwebuga–Mukasa et al., "Repopulation of a human alveolar matrix by adult rat type II pneumocytes in vitro. A novel system for type II pneumocyte culture." *Exp. Cell Res.* (1986) 162(2):423–435.
Gonzalez, et al., "Characterization and Utility of a Monoclonal Antibody Specific to the Apical Surface of Human Alveolar Type 1 Cells," *Am. J. Resp. Crit. Care Med.* 151(4):A169 (Apr. 1995).
Newman, et al., "HT156, An Integral Apical Membrane Protein of the Human Alveolar Type I Cell, is a Biochemical Marker of Acute Lung Injury," *Am. J. Resp. Crit. Care Med.* 157:A16 (Mar. 1998).

\* cited by examiner

*Primary Examiner*—Patrick Nolan
(74) *Attorney, Agent, or Firm*—Carol L. Francis; Paula A. Borden; Bozicevic, Field & Francis LLP

(57) ABSTRACT

The invention features a monoclonal antibodies specific for human type I alveolar cells or for human type II alveolar cells. The invention also features methods of detecting lung injury in a subject using these monoclonal antibodies.

7 Claims, 2 Drawing Sheets

*µg of HLH containing equivalent amount of $HTI_{56}$

*µg of HLH containing equivalent amount of $HTI_{56}$

US 6,284,474 B1

DETECTION AND DIAGNOSIS OF CONDITIONS ASSOCIATED WITH LUNG INJURY

STATEMENT REGARDING FEDERALLY SPONSORED RESEARCH

This invention was made with government support under grant no. HL-41958, awarded by the National Institutes of Health. The government may have certain rights in this invention.

FIELD OF THE INVENTION

This invention relates generally to the field of diagnosis and detection of conditions associated with lung injury and pathology.

BACKGROUND OF THE INVENTION

The lung is a cellularly complex organ that contains more than sixty morphologically distinct types of cells (Stone (1992), Am. J. Respir. Cell Mol. Biol. 6:235–43). These include but are not limited to airway cells (e.g., basal cells, ciliated cells, goblet cells, serous cells, non-ciliated "Clara" cells), smooth muscle cells, chondrocytes, endothelial cells (with differing functional properties depending on the type of blood vessel), circulating blood cells, alveolar macrophages, and interstitial cells. The alveolar portion of the lung contains more than 99% of the internal surface area of the lung and is responsible for the essential function of gas exchange between the air and blood compartments. There are two types of alveolar epithelial cells (whose apical surfaces are on the air side of the alveolar surface), called type I and type II cells.

Type I alveolar cells comprise approximately ninety-eight percent of the interstitial surface area of the lung. Type I cells are extremely thin and are primarily responsible for gaseous diffusion between the airspace and the lung capillaries, as well as for the clearance of liquid from the airspaces. The remaining portion of the alveolar surface is primarily composed of type II alveolar cells. Type II cells have several known functions, including production of pulmonary surfactant, production of immunoeffector substances, transport of ions, and repair of the injured alveolus.

Lung injury is often associated with disturbance and destruction of type I alveolar cells; in particular, injury of the alveolar epithelial barrier is thought to be of central importance in the pathogenesis of acute lung injury. For example, type I cells are involved in the earliest changes in the lung in adult respiratory distress syndrome (ARDS). Within a few hours of onset of ARDS the type I alveolar cells swell and become detached from the alveolus' underlying basement membrane, leaving the gas exchange barrier denuded and prone to leakage of edema fluid. Upon injury to type I cells, type II cells proliferate, spread along the alveolar surface, and eventually differentiate into type I cells.

Methods for early detection and diagnosis of lung injury would greatly benefit patients who have conditions or diseases that are not otherwise detectable using conventional methodology until it is almost too late for successful therapeutic intervention. For example, there are between 30,000 to 100,000 cases annually of ARDS in the U.S. Unfortunately, clinical identification of patients who have developed the syndrome is difficult. Most often, ARDS patients are not identified until the syndrome is full-blown. ARDS is a serious, life-threatening condition in which patients remain critically ill in intensive care units for protracted periods of time. The high mortality in ARDS (approx. 50%) has been unchanged from the initial time of the syndrome's description over twenty years ago.

The presently accepted methods of assessing lung injury require the clinician to obtain biopsy specimens of the lung. The utility of lung biopsy methods in clinical medicine is limited. For example, the invasive nature of the biopsy procedure largely precludes repeated measurements. Interpretation of single biopsies is complicated since lung pathology is often patchy in nature and the size of the biopsy specimen is small. Furthermore, it is difficult to analyze the status of the alveolar epithelial cells obtained at biopsy without time-consuming and costly techniques of electron microscopy. Because electron microscopy is not routinely performed on biopsied lung samples, knowledge about alveolar cells in states of disease is further limited. A non-invasive method for lung injury detection would allow clinicians to make more reliable and accurate diagnoses, monitor the progress of patients, and determine the efficacy of a selected therapeutic regimen, and allow for adjustment and monitoring of therapy.

Unfortunately, the development of diagnostic assays and early therapeutic intervention has been greatly hampered by the lack of human lung cell-specific markers. Specifically, the identification of human type I or type II alveolar cell markers and antibodies that specifically bind such markers has been largely unsuccessful. For example, previously described antibodies that bind to human type I or human type II alveolar cells also bind other alveolar cells and/or bind non-lung tissues (e.g., previously described anti-human type I cell antibodies also bind surface epithelium of distal bronchioles, submucosal glands, skin (superficial keratinocytes), salivary glands, pancreatic acini, breast, prostate, adrenal cortex, and blood vessels (see Singh et al. (1993) Micro. Res. Tech. 26:357–65); previously described anti-human type II cell antibodies also bind to cells found in renal epithelial, Clara cells (airway cells), and cells of other organs (see Singh et al. (1985) Clin Exp. Immunol. 60:579–85; Kotas et al. (1991) Ped. Pulmunol. 10:260–6; Sahali et al. (1993) Am. J. Pathol. 142:1654–67)). Due to the cross-reactivity of such previously described antibodies, these antibodies have only limited uses in, for example, in vitro and in vivo specific and sensitive diagnostic methods for lung disease. Previously identified markers for rodent type I alveolar cells (Dobbs et al. (1988) Biochimica Biophysica Acta 970:146–56) do not cross-react with human cells as determined by morphological and biochemical criteria, making them useless in human applications.

Biochemical and molecular markers for other tissues have proven invaluable in both diagnosis and management of human disease. For example, the biochemical and molecular markers available for cardiac injury (e.g., acute myocardial infraction and ischemia) have been used in cardiac disease to identify when cardiac injury has occurred, to quantitate the extent of injury, and to determine whether there is ongoing injury. Quantitation of injury has also been extremely important in evaluating the therapeutic strategies to treat injury. The potential value of human lung cell markers has been validated in various models of rodent lung injury, in which the airspace liquid content of RT140, a rat type I cell integral membrane protein, correlated directly with the extent of epithelial injury assess by morphologic criteria ((1995) Am. J. Physiol. 268:L181–6; (1997) Am. J. Physiol. 272:L631–8). The lack of analogous markers for human lung injury has greatly impaired the clinician's ability to determine whether lung injury exists, what the prognosis might be, or to determine whether specific therapeutic intervention is of benefit.

The ability to identify patients having lung injury, detect injury at the time of its development, and determine the severity of injury would greatly aid in the early detection of conditions associated with lung injury such as ARDS, and the treatment of such patients before it is may be too late for the patient to benefit. Moreover, a non-invasive method to detect lung injury would provide a more reliable and accurate diagnosis, and allow clinicians to follow a patient's progress and adjust therapy accordingly. Therefore, there is a distinct need in the field for markers for lung injury, especially for acute lung injury, and for methods to readily detect such markers. The present invention addresses this problem.

SUMMARY OF THE INVENTION

The invention features monoclonal antibodies specific for human type I alveolar cells or for human type II alveolar cells. The invention also features methods of detecting lung injury in a subject using these monoclonal antibodies.

Accordingly, in one aspect the invention features methods for detection of lung injury in a human subject, the method comprising the steps of: a) contacting a specific anti-human type I or type II alveolar cell monoclonal antibody (MAb) with a test sample from a subject suspected of having lung injury, wherein the sample is suspected of comprising a human type I or type II alveolar cell-specific polypeptide; and b) detecting binding of the monoclonal antibody to the human type I or type II alveolar cell-specific polypeptide in the sample, where detection of binding of the MAb to the human type I or type II alveolar cell-specific polypeptide in the sample at a level substantially altered relative to a level in a normal subject is indicative of lung injury in the subject. In a preferred embodiment, the polypeptide for human type I or type II alveolar cells may be either HTI56 or HTII280, respectively. In preferred embodiments, the test sample is an edema fluid sample, a plasma sample, or a urine sample.

In an especially preferred embodiment, detection of MAb binding to the type I or type II alveolar cell-specific polypeptide is accomplished by immobilizing polypeptides in the test sample on a solid support; contacting the immobilized polypeptides with the anti-human type II alveolar cell-specific monoclonal antibodies, wherein the antibody is detectably labeled; and detecting binding of the specific monoclonal antibody using a luminometer.

In other aspects, the invention features human type I and type II cell-specific MAbs. The MAbs of the invention can be produced by immunizing a non-human mammal with isolated human type I or type II alveolar cells; producing a hybridoma cell from spleen cells of the immunized mammal; and identifying a hybridoma cell producing an anti-human type I ro type II alveolar cell antibody by specific binding of hybridoma supernatant to human type I or type II alveolar cells in a cytospin preparation or tissue, where the anti-type I or type II alveolar cell MAbs produced are characterized by specific binding to type I or type II alveolar cells, respectively, specific binding to lung tissue, and substantially no detectable binding to tissue homogenates of brain, skin, trachea, lung, esophagus, stomach, intestine, urinary bladder, blood, kidney, or spleen as detected by Western blot. In preferred embodiments, the anti-type I cell MAb binds a polypeptide of about 55–56 kDa (e.g., HTI56); the anti-type II cell MAb binds a polypeptide of about 240–280 kDa (e.g, HTII280).

The invention also features kits useful in detection of lung injury in a subject, the kit comprising a MAb specific for human type I alveolar cells or for human type II alveolar cells.

The invention further features isolated HTI56 and HTII280 polypeptides.

A primary object of the invention is to provide a non-invasive method (e.g., without lung biopsy) for detecting lung injury, which in turn allows for diagnosis of a variety of conditions or diseases associated with such lung injury.

One advantage of the invention is that it provides specific markers for human type I and type II alveolar cells, which markers can be used in a variety clinical situations such as diagnosis of the extent of lung injury due to various processes (e.g., ARDS, infection, inflammatory lung disease), assessment of the state of maturity of fetal lungs, targeting of drugs for delivery to specific cells or to specific regions of the lung, and treatment of diseases such a *Pneumocystis carinii*, in which the pathogen attaches to alveolar cells.

Another advantage is that lung injury detection method of the invention can be used with biological samples such as lung fluid edema, blood and blood-derived samples, and urine, which do not involve invasive techniques (e.g., lung tissue biopsy).

These and other objects, advantages and features of the present invention will become apparent to those persons skilled in the art upon reading the details of the methodology and compositions as more fully set forth below.

DESCRIPTION OF THE PREFERRED EMBODIMENTS

Figure 1:
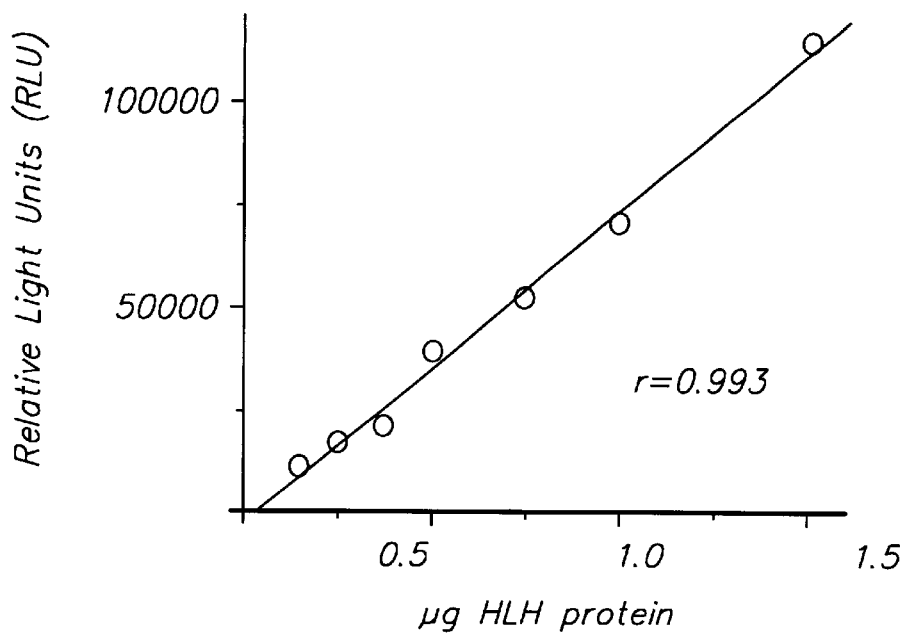
FIG. 1 is a graph showing a standard curve for the HTI56 polypeptide content of human lung homogenate (HLH).

Before the present method and compositions for diagnosis and detection of conditions associated with lung injury are described, it is to be understood that this invention is not limited to the particular methodology, protocols, cell lines, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a hybridoma cell" includes a plurality of such cells and reference to "the antibody" includes reference to one or more antibodies and equivalents thereof known to those skilled in the art, probes that bind the human type I- or type II-specific polypeptides described here, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

The term "antibody" is meant to include complete antibodies, as well as fragments thereof (e.g., F(ab')$_2$, Fab, etc.) and modified antibodies produced therefrom (e.g., antibodies modified through chemical, biochemical, or recombinant DNA methodologies), with the proviso that the antibody fragments and modified antibodies retain antigen binding characteristics sufficiently similar to the starting antibody so as to provide for specific detection of antigen.

By "lung injury associated with abnormal levels of type I cell-specific polypeptide or type II cell specific-polypeptide" is meant damage to the alveolar epithelium. Such lung injury may be distinguished from other forms of lung injury that involve damage to only another compartment, such as to bronchial smooth muscle cells in vascular endothelium.

By "acute lung injury" is meant a clinical syndrome described by the acute onset of arterial hypoxemia and bilateral pulmonary infiltrates.

By "polypeptide marker" is meant a polypeptide or a polypeptide epitope that is substantially only associated with a given cell type. For example, a polypeptide marker of a type I alveolar cell is a polypeptide or polypeptide epitope (e.g., a three-dimensional polypeptide configuration that is bound by a monoclonal antibody) that is substantially only present on the surface of type I alveolar cells.

By "type I cell-specific polypeptide" and "type II cell-specific polypeptide" is meant a polypeptide that is expressed preferentially by, substantially only by, overexpressed on, or otherwise a polypeptide marker for type I alveolar cells and type II alveolar cells, respectively.

"Polypeptide" is meant to encompass naturally-occurring polypeptide molecules, as well as polypeptides that are altered relative to a naturally-occurring polypeptide molecule as a result of insertion, deletion, and/or addition of amino acid residue(s), and/or chemical or biochemical modification (e.g., relative glycosylation states, PEGylation, truncation, radiolabeling, fragments (e.g., fragments of about 8 amino acids, usually at least about 12 amino acids, more usually about 20 amino acids, generally about 50 to 100 amino acids, up to about 90–95% of the full-length polypeptide, etc.).

OVERVIEW OF THE INVENTION

The present invention is based upon the discovery of monoclonal antibodies (MAbs) specific for human type I an type II alveolar cells. Prior to the present invention, efforts to produce such human lung-specific MAbs using conventional methods (e.g., by immunization of animals with lung homogenate) had not been successful. The present inventors found that lung cell-specific MAbs can be produced by immunization with lung cells isolated using a special technique. The MAbs to the alveolar epithelial cell-specific polypeptides HTI56 and HTII280 (which are specific for human type I and type II alveolar cells, respectively) are examples of MAbs identified using this method. The HTI56 and HTII280 identified by the MAbs of the invention have been isolated and characterized.

The inventors have also discovered that the human type I- and type II-specific MAbs can be used to detect very small amounts of their respective polypeptides in test samples, and that the detection of these proteins in test samples (e.g., lung edema fluid, bronchoalveolar lavage, blood (e.g., serum, plasma, etc.), or urine) is indicative of lung injury in the subject from whom the sample was obtained.

ISOLATION OF HUMAN TYPE I OR TYPE II CELLS

The present inventors have discovered a technique for human type I and type II alveolar cell isolation. The type I and type II alveolar cells isolated using the inventors' method can then be used as the immunogen in production of antibodies that specifically bind type I or type II alveolar cells, as well as in the study and characterization of type I and type II cells.

Isolation of human type I and type II cells generally requires immediate processing of lung samples resected at surgery. Common practice for cell isolation and organ culture (including tracheal and airway epithelium) is to process tissue stored for up to 48 hours. Although this practice is successful for tracheal and airway epithelium, it is not possible for the isolation of alveolar epithelial type I cells since these cells disintegrate if the lung is stored. Thus, immediate processing is essential for successful isolation of cells since alveolar epithelial cells undergo rapid necrosis. In general, immediate processing means that type I or type II alveolar cells are isolated from the lung sample within about 1 hour after resection, and usually no more than about 2 hours, providing that the lung sample is kept on ice.

The lung sample may be perfused to remove blood (e.g., plasma and blood cells). The lung sample is then washed to remove mucous and/or other secretions by, for example, lavage with a substantially pH-neutral, buffered salt solution, preferably one free of calcium and magnesium (e.g., $Ca^{++}Mg^{++}$-free phosphate-buffered saline (PBS) containing EDTA and EGTA). The lung sample is then instilled with tissue culture media (e.g., RPMI 603, RPMI 1634, RPMI 1640, preferably RPMI 1640). The tissue culture media comprises a protease that facilitates cell separation without substantial degradation of cell surface proteins (e.g., elastase) and a biocompatible polymer that facilitates preservation of type I and type II cell integrity (e.g., glucan polymers (e.g., polysaccharides), polyethylene glycol, etc., most preferably dextran). In general, for isolation of type I cells the amount of protease present in the media is greater than for isolation of type II cells (e.g., about 80 U/ml elastase for type I cell isolation compared to about 40 U/ml elastase for type II cell isolation). The enzyme-instilled lung sample is incubated for a time and at a temperature sufficient to facilitate separation of lung cells without substantial loss of type I and/or type II cell integrity, generally at least about 30 min, preferably at least about 45 min, more preferably at least about 1 hr. Additional solution may be added to the lung sample during this period in order to keep the lung sample segment inflated. The lung sample is then minced, the lung sample fragments washed, and the sample filtered.

Type I and/or type II alveolar cells are separated from the sample using conventional means. Preferably, type I cells are isolated using a density gradient (e.g., a Percoll density gradient). For isolation of type II cells the sample is preferably processed to remove macrophages and lymphocytes (e.g., by contacting the sample with plastic support (e.g., a Petri dish) coated with an antibody comprising an Fc portion). The unbound cells were then separated from the supernatant using conventional means, e.g., a density gradient, such as a metrizamide, albumin, sucrose, or Percoll density gradient, preferably a Percoll density gradient. Fractions containing type II cells can be identified by cytocentrifugation of the fraction and staining with modified Papanicolaou stain, which stain only type II cells (see, e.g., Dobbs (1990) *Am. J. Physiol.* 258(4 Pt 1):L134–L147).

PRODUCTION OF ALVEOLAR EPITHELIAL CELL-SPECIFIC ANTIBODIES

Antibodies that specifically bind human type I or type II alveolar cells are produced by: 1) isolation of human type I cells or type II cells as described above; 2) immunization of non-human animals with the isolated cells and production of hybridomas; and 3) identification of antibodies that specifically bind either type I or type II alveolar cells (e.g., by screening hybridoma supernatants for binding to type I or type II alveolar cells in cytospin preparations). Each of these steps are described below.

Immunization of Non-human Animals with Isolated Type I or Type II Cells and Production of Hybridoma Cells Antibodies specific to human type I or type II alveolar cells are produced by immunizing a non-human mammal (e.g., mouse) with isolated human type I or type II alveolar epithelial cells. Immunization with isolated human type I or type II alveolar epithelial cells was found to be necessary since immunizations with homogenates of human lung were not successful in producing monoclonal antibodies specific to human alveolar epithelial cells.

Immunization and hybridoma production with the isolated human type I or type II cells can be accomplished according to conventional methods well known in the art. Preferably, type I or type II cell-containing fractions from the Percoll density gradient described are used for immunization. The immunized animal is an immunocompetent, non-human mammalian host, including murine, rodentia, lagomorpha, ovine, porcine, bovine, etc. is immunized with human type I or type II cells isolated as described above. The choice of a particular host is primarily one of convenience. Immunizations are generally performed in accordance with conventional techniques, where the isolated cells may be injected subcutaneously, intramuscularly, intraperitoneally, intravascularly, etc.

Normally, from about $10^6$ to $10^8$ cells, preferably about $10^7$ cells, will be used, which may be divided up into 1 or more injections, usually not more than about 8 injections, over a period of from about one to three weeks. The injections may be with or without adjuvant, e.g. complete or incomplete Freund's adjuvant, specol, alum, etc.

Either monoclonal or polyclonal antibodies, preferably monoclonal antibodies (MAbs), are produced from the immunized animal. Polyclonal antisera may be harvested from serum in accordance with conventional methods after completion of the immunization schedule. For production of MAbs, lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Methods for hybridoma production are well known in the art (see, e.g., *Antibodies, A Laboratory Manual*, Harlow & Lane eds., (1988) Cold Spring Harbor Press).

Screening of Hybridomas for Production of Type I- or Type II-specific Antibodies Hybridomas may be screened for production of anti-type I or anti-type II cell-specific MAbs by contacting hybridoma supernatants with isolated type I or isolated type II cells, respectively. Preferably, the type I and/or type II cells used for screening are prepared in a manner that substantially preserves the cell surface structure, e.g., by use of cytocentrifuged preparations of isolate type I and/or type II cells, or use of cryostat sections of human lung tissue. Cytocentrifuged preparations are preferred as this method will allow for more efficient screening. Hybridoma supernatants may also be screened for the ability to specifically bind substantially purified type I- or type II-specific polypeptides (e.g., HTI56 or HTII280, respectively) or fragments of such polypeptides that are capable of presenting the desired epitope.

Of particular interest is the human type I alveolar cell-specific MAb produced by the hybridoma cell ATCC accession no. HB-12519, as well as cross-reactive antibodies (i.e. those which bind to the same epitope, and substantially inhibit simultaneous binding), species analogs thereof, binding fragments thereof, and conjugates thereof. Also of particular interest is the human type II alveolar cell-specific MAb produced by the hybridoma cell ATCC accession no. HB-12520, as well as cross-reactive antibodies (i.e. those which bind to the same epitope, and substantially inhibit simultaneous binding), species analogs thereof, binding fragments thereof, and conjugates thereof. A deposit of the murine hybridoma cell lines ATCC accession no. HB-12519 and ATCC accession no. HB-12520 was made at the American Type Tissue Collection, 10801 University Boulevard, Manassas, Va. 20110-2209, on Apr. 22, 1998.

Modification of Type I- and Type II-specific MAbs

The antibodies and MAbs of the present invention can be modified in any of a variety of ways, with the proviso that the modified MAbs retain substantially specific binding to the original antigen (e.g., to the original type I- or type II-specific polypeptide (e.g., HTI56 and HTII280, respectively)). The ability of such modified antibodies to specifically and sensitively bind their original antigen can be assessed in in vitro assays as described herein (e.g., to assess binding of the modified antibodies to type I or type II cells in cytospin preparations, to type I or type II cell-specific polypeptides (e.g., HTI56 or HTII280) in ELISA assays, etc.). Such screening is routine and, with the guidance provided herein, within the skill of the ordinarily skilled artisan.

Modified antibodies contemplated by the present invention include those produced modified using biochemical, chemical, or recombinant DNA techniques. For example, antibody fragments, such as Fv, F(ab')$_2$ and Fab may be prepared from the antibodies of the invention by cleavage of the intact protein, e.g. by protease or chemical cleavage. Alternatively, a truncated gene is designed. For example, a chimeric gene encoding a portion of the F(ab')$_2$ fragment would include DNA sequences encoding the $C_{H1}$ domain and hinge region of the H chain, followed by a translational stop codon to yield the truncated molecule. Preferably, such antibody fragments retain antigen avidity and/or affinity that is substantially the same as the original antibody from which they are derived.

The subject antibodies may also be produced as a single chain, instead of the normal multimeric structure. Single chain antibodies are described in Jost et al. (1994) *J. Biol. Chem.* 269:26267–73, and others. DNA sequences encoding the variable region of the heavy chain and the variable region of the light chain are ligated to a spacer encoding at least about four amino acids of small neutral amino acids, including glycine and/or serine. The protein encoded by this fusion allows assembly of a functional variable region that retains the specificity and affinity of the original antibody.

The antibodies of the invention may also be humanized. Methods of humanizing antibodies are well known in the art. The humanized antibody may be the product of an animal having transgenic human immunoglobulin (Ig) constant region genes (see for example International Patent Applications WO 90/10077 and WO 90/04036). Alternatively, the antibody of interest may be engineered by recombinant DNA techniques to substitute the $C_{H1}$, $C_{H2}$, $C_{H3}$, hinge domains, and/or the framework residues with the corresponding human sequence (see WO 92/02190). Humanized antibodies are of particular interest for in vivo use in humans (e.g., for use in diagnostic imaging, therapy, etc.).

The antibodies of the invention may also be used to produce chimeric antibodies. The use of Ig cDNA for construction of chimeric Ig genes is known in the art (Liu et al. (1987) *Proc. Natl. Acad. Sci.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The chimeric, humanized antibody is then expressed by conventional methods.

Expression vectors for use in modification of the antibodies of the invention are well known in the art and include plasmids, retroviruses, YACs, EBV derived episomes, and the like. For example, where the anti-type I or anti-type II alveolar cell-specific antibody is to be modified to provide a human antibody heavy and/or light chain constant region, a convenient vector is one that encodes a functionally complete human $C_H$ or $C_L$ Ig sequence, with appropriate restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Biol.* 3:280), Rous sarcoma virus LTR (Gorman et al. (1982) *Proc. Natl. Acad. Sci.* 79:6777), and Moloney murine leukemia virus LTR (Grosschedl et al. (1985) *Cell* 41:885); native Ig promoters, etc.

Of particular interest is the modification of the antibodies to provide for detectably labeled antibodies. Exemplary detectable labels that allow for direct measurement of antibody binding include radiolabels (such as $^3$H or $^{125}$I), fluorophores, dyes, magnetic beads, chemiluminescers, colloidal particles, and the like. Examples of labels which permit indirect measurement of binding include enzymes where the substrate may provide for a colored or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, e.g. phycoerythrin and allophycocyanins; fluorescein and Texas red), which can be used with a fluorescence activated cell sorter; haptens; and the like. Preferably, the detectable label allows for direct measurement in a plate luminometer, e.g., biotin.

Also of particular interest is the modification of the antibodies of the invention to provide for antibodies useful in in vivo diagnosis or in therapy, e.g., in the delivery of a therapeutic agent to the alveolus via specific binding to type I or type II alveolar cells. Antibody modification and use of such modified antibodies these applications of the invention are described in more detail below.

Uses of Type I- and Type II-alveolar Cell Specific Antibodies

The antibodies of the present invention can be used in a variety of applications including, but not limited to, in vitro and in vivo detection and diagnosis of lung injury in a subject, isolation and purification of type I or type II alveolar cell-specific polypeptides, isolation of the specific antigen to which the MAbs bind (e.g., HTI56 and HTII280), isolation of the specific lung cell types with which the lung cell-specific proteins are associated (e.g., immunoselection of type I and type II alveolar cells), identification of specific lung cell types in a tissue sample (e.g., in an in vitro assay of a tissue biopsy or in an in vivo assay to provide an image of the lung isolation of type I or type II alveolar cells), delivery of a therapeutic agent to the alveolus, for production of anti-idiotypic antibodies for use in therapy (e.g., to block binding of infectious agents to type I or type II alveolar cells), and other uses that will be readily apparent to the ordinarily skilled artisan upon review of the present specification. Exemplary in vitro and in vivo uses of the antibodies of the invention are described in more detail below.

DETECTION OF LUNG INJURY USING ANTI-TYPE I AND ANTI-TYPE II ALVEOLAR CELL ANTIBODIES

The antibodies of the invention can be used for in vitro and in vivo detection and diagnosis of lung injury in a subject. In general, the in vitro assays contemplated by the invention involve contacting a test sample from a subject suspected of having lung injury. The test sample may be any appropriate biological sample in which a type I and/or type II cell-specific polypeptide marker can be detected. Such test samples include, but are not necessarily limited to lung edema fluid, bronchoalveolar lavage sample, blood or blood-derived samples, (e.g., plasma, serum, etc.), and urine. Detection of binding of the anti-type I or anti-type II cell-specific polypeptide in the sample at a level elevated relative to a level in a normal subject is indicative of lung injury in the subject. The in vitro assay may be performed either qualitatively or quantitatively. The in vitro methods and compositions disclosed herein can be also used to examine biopsy or pathological lung tissue in order to determine the extent and type of lung injury. The in vivo detection and diagnosis method of the invention involves administration of a detectably labeled anti-type I or anti-type II alveolar cell MAb to a subject and detection of binding of the labeled MAb in the lung of the subject.

Each of these variations of the detection and diagnostic assays of the invention are described below in more detail.

In Vitro Methods of Lung Injury Detection

Samples for Use in the in Vitro Assay

Any sample that is suspected of containing a alveolar epithelial cell-specific protein as described herein, in which detection of the alveolar epithelial cell-specific protein is indicative of lung injury. Exemplary samples suitable for use in the in vitro detection assay of the invention include, but are not necessarily limited to, fluid obtained from lung (e.g., lung edema fluid, bronchoalveolar lavage fluid, etc.), blood or derivatives thereof (e.g., whole blood, plasma, serum, etc.), biopsies (e.g., frozen or fixed tissue), etc. Preferably the sample is blood or a blood-derived sample, or a sample of pulmonary edema fluid, more preferably blood or a derivative thereof, most preferably plasma.

In Vitro Detection Methods

In vitro methods for detection of lung injury involve the detection of binding between a type I cell- or type II cell-specific MAb of the invention and a type I cell- or type II cell-specific polypeptide (e.g., HTI56 and HTII280, respectively) in a patient sample, where the presence of specific binding is indicative of lung injury. The detection of type I cell- or type II cell-specific polypeptide in a sample or fraction thereof may be accomplished by a variety of specific assays, and may be performed either qualitatively or quantitatively. In general, the assay will measure the reactivity between a MAb of the invention and a patient sample, usually a sample of lung fluid or a blood-derived sample, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, PBS, etc.

In one embodiment, a conventional sandwich type assay is used. A sandwich assay is performed by first immobilizing proteins from the test sample on an insoluble surface or support. The test sample may be bound to the surface by any convenient means, depending upon the nature of the surface, either directly or indirectly. The particular manner of binding is not crucial so long as it is compatible with the reagents and overall methods of the invention. They may be bound to the plates covalently or non-covalently, preferably non-covalently.

The insoluble supports may be any compositions to which the test sample polypeptides can be bound, which is readily separated from soluble material, and which is otherwise compatible with the overall method of detecting and/or measuring type I cell- or type II cell-specific polypeptide. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

After adding patient samples or fractions thereof, the non-specific binding sites on the insoluble support, i.e. those not occupied by polypeptide, are generally blocked. Preferred blocking agents include non-interfering proteins such as bovine serum albumin, casein, gelatin, and the like Alternatively, several detergents at non-interfering concentrations, such as Tween, NP40, TX100, and the like may be used.

Samples, fractions or aliquots thereof can be added to separately assayable supports (for example, separate wells of a microtiter plate). Preferably, a series of standards, containing known concentrations of human type I-specific polypeptide (e.g., HTI56) or human type II-specific polypeptide (e.g., HTII280) is assayed in parallel with the samples or aliquots thereof to serve as controls and to provide a means for quantitating the amounts of alveolar cell-specific polypeptide present in the test sample. Generally from about 0.001 ml to 1 ml of sample, diluted or otherwise, is sufficient, usually about 2 $\mu$l to 50 $\mu$l sufficing. Preferably, each sample and standard will be added to multiple wells so that mean values can be obtained for each.

After the test sample polypeptides are immobilized on the solid support, anti-type I cell-specific or anti-type II cell-specific MAb is added. The incubation time of the sample and the MAB should be for at time sufficient for MAb binding to the insoluble polypeptide. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, MAb binding to the sample can be detected by virtue of a detectable label on the MAb. Where the anti-type I cell or anti-type II cell MAb is not detectably labeled, MAb binding can be detected by contacting the sample with a solution containing antibody-specific second receptor, in most cases a secondary antibody (i.e., an anti-antibody). The second receptor may be any compound which binds antibodies with sufficient specificity such that the bound antibody is distinguished from other components present. In a preferred embodiment, second receptors are antibodies specific for the type I cell-specific MAb or the type II cell-specific MAb, and may be either monoclonal or polyclonal sera, e.g. goat anti-mouse antibody, rabbit anti-mouse antibody, etc.

The antibody-specific second receptors are preferably labeled to facilitate direct, or indirect quantification of binding. Examples of labels which permit direct measurement of second receptor binding include light-detectable labels, radiolabels (such as $^3$H or $^{125}$I), fluorescers, dyes, beads, chemiluminescers, colloidal particles, and the like. Examples of labels which permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Alternatively, the second receptor may be unlabeled. In this case, a labeled second receptor-specific compound is employed which binds to the bound second receptor. Such a second receptor-specific compound can be labeled in any of the above manners. It is possible to select such compounds such that multiple compounds bind each molecule of bound second receptor. Examples of second receptor/second receptor-specific molecule pairs include antibody/anti-antibody and avidin (or streptavidin)/biotin. Since the resultant signal is thus amplified, this technique may be advantageous where only a small amount of type I cell-specific or type II cell-specific polypeptide is present, or where the background measurement (e.g., non-specific binding) is unacceptably high. An example is the use of a labeled antibody specific to the second receptor. More specifically, where the second receptor is a rabbit anti-allotypic antibody, an antibody directed against the constant region of rabbit antibodies provides a suitable second receptor specific molecule. The anti-Ig will usually come from any source other than human, such as ovine, rodentia, particularly mouse, or bovine.

The volume, composition and concentration of anti-MAb solution provides for measurable binding to the MAb already bound to receptor. The concentration will generally be sufficient to saturate all MAb potentially bound to type I cell-specific or type II cell-specific polypeptide. When antibody ligands are used, the concentration generally will be about 0.1 to 50 $\mu$g/ml, preferably about 1 $\mu$g/ml. The solution containing the second receptor is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing.

After the second receptor or second receptor-conjugate has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

The absence or presence of MAb binding may be determined by various methods that are compatible with the detectable label used, e.g., microscopy, radiography, scintillation counting, etc. Generally the amount of bound anti-type I or anti-type II cell MAb detected will be compared to control samples (e.g., positive controls containing type I cell- or type II cell-specific polypeptides or negative controls lacking such polypeptides). The presence of increased levels of bound anti-type I or anti-type II cell MAb is indicated of increased levels of type I cell-specific (e.g., HTI56) or type II cell-specific (e.g., HTII280) polypeptide, respectively, which in turn is indicative of lung injury in the subject from whom the sample was obtained. Usually at least about a 2-fold increase, often about a 4- to 5-fold increase in the test sample relative to levels of type I cell-specific polypeptide or type II cell-specific polypeptide associated with normal subjects (e.g., subjects that do not have lung injury associated with increased type I cell- or type II cell-specific polypeptide levels) is indicative of lung injury in a subject. The severity of lung injury may be directly correlated with the level of type I cell-specific or type II cell-specific polypeptide in the sample. Furthermore, the level of type I cell-specific or type II cell-specific polypeptide in the sample may vary with the type of lung injury.

In one especially preferred embodiment, alveolar cell-specific proteins are detected using an ELISA dot-blotting light-based assay. The inventors have found that colorimetric ELISAs are generally not sufficiently sensitive or specific to measure type I cell- and type II cell-specific polypeptides such as HTI56 and HTII280 in lung liquid, bronchoalveolar lavage, or plasma. Moreover, quantitation of the alveolar cell-specific polypeptides by light emission method or densitometry on X-ray film is extremely time-consuming, and requires multiple standard curves and multiple exposures for each point measured. While the colorimetric, light emission, and densitometry variations of the assay of the invention may be useful for qualitative results and/or for use in certain contexts, the use of the ELISA dot-blotting light-based assay is presently the best and most preferred means of carrying out in vitro detection of the type I cell- and type II cell-specific polypeptides of the invention.

The ELISA dot-blotting light-based assay is preferably carried out by immobilizing the proteins present in the test sample on a solid support (e.g., by dot blotting the sample onto nitrocellulose). After quenching the dot-blotted sample for endogenous peroxidase activity and blocking non-specific binding, the samples are then incubated with type I cell- or type II cell-specific MAb for a period sufficient for MAb binding (e.g., usually not more than 20 mins). The samples are washed to remove unbound MAb, and incubated with a solution containing horse radish peroxidase (HRP)-labeled secondary antibody (e.g., HRP-labeled sheep anti-mouse antibody). After washing to remove unbound secondary antibody, the samples are treated with a solution containing luminlol (ECL Light Detection System, Amersham). Bound secondary antibody, which is indicative of bound MAb, is detected in a plate luminometer. Binding of secondary antibody may also be detected by autoradiography. This embodiment of the invention provides a highly-sensitive assay with low background levels, and allows quantitation of each alveolar cell-specific polypeptide in as little as 2–50 $\mu$l of sample. The method is far less time consuming and about 20 to 50 times more sensitive than scanning densitometry, calorimetric ELISA assays, or Western blotting.

Variations of the preferred embodiment of the in vitro detection assay of the invention as described above will be readily apparent to the ordinarily skilled artisan. For example, a competitive assay may be used. In addition to the patient sample, a competitor to the type I cell-specific or type II cell-specific polypeptide is added to the reaction mix. The competitor and the alveolar cell-specific polypeptide compete for binding to the MAb. Usually, the competitor molecule will be labeled and detected as previously described, where the amount of competitor binding will be proportional to the amount of type I cell- or type II cell-specific polypeptide present in the sample. The concentration of competitor molecule will be from about 10 times the maximum anticipated alveolar cell-specific concentration to about equal concentration in order to make the most sensitive and linear range of detection.

Another alternative protocol is to provide anti-type I cell or anti-type II cell MAb bound to the insoluble surface. After immobilization of the MAb on the insoluble support, the test sample, the samples incubated to allow MAb-polypeptide binding, and binding detected using a second anti-type I cell- or anti-type II cell-specific polypeptide antibody.

In yet another alternative embodiment, the detection assay may be carried out in solution. For example, the anti-type I cell or anti-type II cell MAb is combined with the test sample, and immune complexes of MAb and alveolar cell-specific polypeptide are detected. Other immunoassays (e.g., Ouchterlony plates or Western blots may be performed on protein gels or protein spots on filters) are known in the art and may find use as diagnostics.

Although not a preferred embodiment, the in vitro detection assay of the invention can also be carried out by staining cells in histological sections with labeled antibodies, performed in accordance with conventional methods.

In Vivo Methods of Lung Injury Detection

The MAbs of the invention can be used in vivo as diagnostic imaging reagents. The MAbs for use in accordance with this aspect of the invention are preferably detectably labeled with a detectable label that can be detected from outside the subject's body using any of a variety of conventional imaging techniques. It may be preferably to use humanized versions of the MAbs of the invention, so as to avoid any side-affects that may be associated with administration of non-human antibodies to the patient.

The MAbs of the invention can be used in connection with any suitable conventional imaging technique that is amenable to use with detectably labeled antibodies. Such methods include, but are not necessarily limited to, positron emission tomography (PET), radioimmunodetection, and the like. For a review of imaging with antibodies, see, e.g., Goldenberg (1997) *Cancer* 80(12 Suppl):2431–5; Shaffer (1997) *Hematol. Oncol. Clin. North Am.* 11(2):197–213; Weynants (1997) *Eur. Respir. J.* 10(8):1703–19; and Salvatori (1997) *Rays* 22(22):51–72.

Modifications of the In Vitro and In Vivo Assays of the Invention

The ordinarily skilled artisan will readily appreciate that the in vitro and in vivo detection assays described herein can be modified in a variety of ways that are consistent with the spirit of the invention. For example, the assays of the invention may be used to quantify the extent and duration of alveolar epithelial injury, to predict impending lung injury, and to assess the efficacy of therapeutic modalities. The assays of the invention can also be adapted to the study of normal lung functions, fetal lung development, response of the lung to injury, and the mechanisms important in lung repair as well as the treatment useful for aiding lung repair and/or development. The assays may be performed with either an anti-type I cell or anti-type II cell MAb, with both an anti-type I cell and an anti-type II cell MAb, and/or with other antibodies (e.g., against other specific types of lung cells) that may be helpful in diagnosis and/or therapy of lung disease. It may be that comparison of a battery of different proteins (e.g., HTI56, HTII280, and other known or as yet-unidentified molecules specific to other cell types) will permit detailed analysis of the lung structures that are injured. For example, comparison of the presence of HTI56 and HTII280 may be important in determining the extent of lung injury, with HTII280 being more abundant in severe lung injury. Alternatively, certain diseases may be associated with damage to one alveolar cell type and not the other (e.g., damage to type I cells but not type II cells).

Furthermore, the in vitro and in vivo diagnostic methods, as well as the drug-delivery methods, of the invention may be accomplished using type I and/or type II alveolar cell-specific polypeptide markers, and antibodies specific for such markers, other than or in addition to those polypeptide markers and antibodies described herein. For example, a type I cell-specific marker that may be useful in the diagnostic methods of the invention may be a human analogue of the rat type I cell-specific marker RT140 (T1α)(OTS-8) (gp38) (Nose et al. (1990) *Cell Growth Differ.* 1:511–8; Zimmer et al. (1997) *Biochem. J.* 326:99–108) or rat aquaporin 5 (Nielsen et al. (1997) *Am. J. Physiol.* 273:C1549–61). Although other polypeptide markers may not be absolutely specific for type I or type II alveolar cells, they may prove adequately substantially specific for type I and/or type II cells, and thus prove useful in measurement of lung injury using the methods of the invention, although markers with less specificity may, of course, provide less specific information. However, these markers may be useful when used in combination with other less-specific markers and/or with the more specific polypeptide markers described herein (e.g., HTI56, HTII280).

The diagnostic and/or drug-delivery (e.g., therapeutic) methods of the invention may also be practiced with markers specific for lung cells other than type I or type II cells. For example, the methods and compositions described herein may be modified to facilitate isolation of other specific types of lung cells, production of hybridomas, and identification of hybridomas secreting a selected lung cell-specific antibody. These lung cell-specific antibodies may be useful, either alone or in combination with the type I cell-specific and/or type II cell-specific antibodies described herein. One of ordinary skill in the art will readily appreciate that such lung cell-specific polypeptide markers and antibodies specific for such markers are contemplated by the invention, and may be obtained through modification of the methods and compositions described herein. Furthermore, such lung-cell specific polypeptide markers and antibodies, either alone or in combination with the type I cell- and type II cell-specific markers described herein, may prove especially useful in the diagnostic methods of the invention, e.g., in the identification of individuals having lung injury.

Kits for in Vitro and in Vivo Lung Injury Detection Assays

The MAbs of the invention can be provided in a convenient kit for use by the clinician or in laboratories to detect the presence of type I cell- or type II cell-specific antibodies in patient samples. In such kits the MAb(s) is provided in a labeled container; the MAb(s) can be detectably labeled with a detectable label suitable to the method for which the kit is supplied. For in vitro detection assays, the kit can also include a solid support for immobilization of the polypeptides in a test sample, which solid support may also have control regions having pre-bound type I cell- or type II cell-specific polypeptides for use as a positive control and/or as a standard for quantitating alveolar cell-specific polypeptides in the sample. In a preferred embodiment, the solid support and MAb are provided in a form suitable for use in the light-based ELISA detection methods of the preferred embodiment of the invention. The kit may also include specific instructions for performing the assay, as well as information regarding the characteristics of positive and negative samples.

It may be especially convenient to provide the kit in the form of a self-contained apparatus in which the in vitro assay of the invention can be performed. A number of such kits and apparatuses are known in the art. For example, the apparatus will generally employ a continuous flow-path of a suitable filter or membrane, having at least two regions, a reagent region and a sample region. The sample region is prevented from fluid transfer contact with the other portions of the flow path prior to receiving the sample. After the sample region receives the sample, and the polypeptides in the sample are immobilized on the sample region surface, the sample region is brought into fluid transfer relationship with the reagent region, thus allowing MAb in the reagent region to contact the sample region. After incubation of the MAb with the test sample for a time sufficient for MAb binding to its specific polypeptide, the amount of MAb binding is detected.

Variations on kits and apparatuses described above will be readily apparent to the ordinarily skilled artisan and are encompassed by the present invention.

ANTIBODY-BASED DELIVERY OF THERAPEUTIC AGENTS TO THE ALVEOLUS

The MAbs of the invention can be used to deliver therapeutic agents in the treatment (e.g., alleviation of symptoms, prophylaxis, etc.) of various lung conditions or diseases (e.g., for treatment of cancer, for delivery of nucleic acid for gene therapy, etc.). For example, the MAbs of the invention can be covalently bound to a therapeutic compound and administered to the patient (e.g., by inhalation, or other means of delivery into the alveolus). The anti-type I cell or anti-type II cell MAb would then bind to its specific target cell, thereby specifically delivering the therapeutic agent bound to it to the alveolus. The amount of therapeuticallymodified antibody to deliver to the subject can be determined through routine methods, and the efficacy of the therapy monitored by any of a variety of means. For example, where the condition to be treated is associated with lung injury, the in vitro assays of the invention can be used to determine the patient's progress and to adjust dosages accordingly. The therapeutic antibody may also be detectably labeled so as to provide for in vivo imaging, thus allowing the clinician to directly monitor and assess delivery of the therapeutic agent to the alveoli.

The antibodies of the invention can also be incorporated into other delivery vehicles to facilitate alveolar-specific delivery. For example, the antibodies of the invention can be incorporated into liposomes, which in turn can contain a drug which is to be delivered to the alveolus. Methods for production of liposomes and incorporation of targeting molecules therein are known in the art.

Methods for such modification of antibodies suitable for delivery of therapeutic agents are well known in the art. For example, where the therapeutic agent to be delivered to the alveolus is a polypeptide, the polypeptide can be associated with the MAb of the invention through biochemical conjugation or using recombinant DNA methodology. The MAbs of the invention can be modified to provide, for example, antibody-drug heterocomplexes, where the drug is a polypeptide or other compound that is desired for delivery to the alveolus. Exemplary drugs that may be delivered to the alveolus include, but are not limited to antimicrobial agents (e.g. antibiotics, antiviral agents, anti-fungal agents, etc.), anti-neoplastic agents, agents that inhibit attachment or adherence of pathogens to type I or type II cells, etc. For example, both *Pneumocystis carinii* and influenza virus A adhere to type I cells during infection. The antibodies of the invention can be coupled to a molecule that prevents binding of the pathogen to the type I or type II cell through, for example, steric hindrance or through antimicrobial action. For a review of antibody-based delivery in the context of cancer therapy, see Weynants et al. (1997) *Eur. Respir. J.* 10(8):1703–19.

The MAbs of the invention can also be used as a template for the production of anti-idiotypic antibodies, which can be used in therapy to, for example, block infection. For example, some lung pathogens (such as *Pneumocystis carinii*, an important pathogen in AIDS) attach specifically to the surfaces of the type I alveolar cells. Direct inhibition of this attachment with antibodies may provide an effective treatment. The MAbs of the invention may also find use as therapeutic agents by direct administration of the unmodified antibody.

The MAbs of the invention may also be used to facilitate instillation of alveolar cells (e.g., to isolate and deliver cells for instillation into the lung to facilitate repair), delivery of cell-specific antigens, and the delivery of cell modulators to the alveolus (e.g., to facilitate and/or accelerate lung repair and to restore normal lung function, e.g., by delivery of substances that facilitate differentiation of type II cells into type I cells). For example, keratinocyte growth factor (KGF), which potentiates proliferation of type II cells, can be delivered to type II cells by conjugating KGF to an anti-type II cell MAB of the invention. Likewise, other factors for promoting proliferation of type I or type II cells, or promoting differentiation of type II cells into type I cells can be delivered using the MAbs of the invention.

LUNG INJURY-ASSOCIATED CONDITIONS AMENABLE TO DIAGNOSIS AND TREATMENT

The methods and compositions described herein can be used in the diagnosis and treatment of any of a variety of conditions or diseases associated with lung injury. For example, conditions and diseases amenable to diagnosis using the methods and compositions of the invention are those conditions and diseases associated with altered levels of type I cell-specific or type II cell-specific polypeptides relative to levels of these polypeptides in normal subjects. For example, a condition such as acute lung injury is associated with an increased level of a type I cell-specific polypeptide (e.g., HTI56) and an increased level of a type II cell-specific polypeptide (e.g. HTII280), while conditions or disease associated with less functioning lung (as in an autoimmune disorder) may be associated with decreased levels of type I cell- and/or type II cell-specific polypeptides.

Exemplary conditions and diseases for diagnosis and treatment using the methods and compositions of the invention may include, but are not limited to, conditions or diseases associated with lung injury resulting from or associated with: inhalation of substances (e.g., toxicants, organic compounds, irritants, pollutants, etc.); mechanical injury (e.g., radiation, blast pressure, scuba diving, etc.), infection (e.g., bacterial infection (e.g., bacterial pneumonia, tuberculosis, Staphylococcus, etc.), fungal infection (e.g., *Pneumocystis carinii*), viral infection, etc.); inflammatory lung diseases or conditions (e.g., asthma); and injury to other organs that may lead to lung injury (e.g., cardiac arrest).

Of particular interest is the detection of conditions associated with acute lung injury. Also of particular interest is the early diagnosis and treatment of adult respiratory distress syndrome (ARDS), emphysema, interstitial fibrosis, bronchiectasis, autoimmune disorders (e.g., lung disease secondary to sclerosis (e.g., progressive systemic sclerosis), systemic lupus erythematosus, rheumatoid lung, and related disorders), neonatal respiratory distress syndrome, and like conditions, including those that involve structural damage to the lung (e.g., after or during infectious disease). The present invention can also be used to assess lung injury or repair after any condition that might affect lung function, such as after cardiopulmonary bypass (in which some lungs are injured in the "postperfusion syndrome"). The present invention can also be used to assess lungs for integrity prior to transplantation, and to monitor the status of the lungs after transplantation. With all of these examples, the measurement of lung injury may be the first step in the design of rationale therapy for the patient, and may be used to identify the modalities that aid in lung repair.

ISOLATION OF TYPE I AND TYPE II ALVEOLAR CELL-SPECIFIC PROTEINS

Alveolar cell-specific polypeptides identified using the methods and/or compositions of the present invention may be purified, concentrated, and/or enriched from the naturally occurring source using any convenient methodology, where a variety of methodologies for protein purification are known in the art. See Guide to Protein Purification (Murray P. Deutscher ed., Harcourt Brace & Co.)(1990). Preferably, the MAbs of the invention are used in the isolation and purification of type I cell- and type II cell-specific polypeptides.

Generally, the purification procedure employed will comprise one or more steps which result in the separation of type I cell- or type II cell-specific polypeptides from at least a portion of the other components of the naturally occurring source from which it is to be purified. Viewed another way, the purification will be any method in which one or more components of the initial sample are separated from the sample so as to enrich the remaining sample with respect to a type I cell- or type II cell-specific polypeptide, i.e. increase the concentration of a type I cell- or type II cell-specific polypeptide in the remaining sample. The purification conditions should be mild so as to avoid denaturation of the polypeptide to be isolated.

The MAbs of the invention can be used to isolate and purify the type I cell- or type II cell-specific polypeptides to which they specifically bind using immunoaffinity or immunoprecipitation procedures. Such methods are well known in the art. For example, immunoaffinity purification is accomplished by first preparing a sample from the naturally occurring source of the polypeptide, e.g. lung edema fluid, lung tissue, etc. Such preparation may involve homogenization of the sample and/or suspension in solution, and subsequently clarification (e.g., by centrifugation) to remove any particulate matter. The solution is then be passed through an affinity column having bound anti-type I cell- or anti-type II cell-specific MAb, which MAb binds alveolar cell-specific polypeptide in the sample. The column is then washed to remove unbound material, and then washed under a different set of washing conditions to promote release of the bound polypeptide from the MAb or release of MAb from the affinity column.

The type I and type II cell-specific polypeptides of the invention can be used in a variety of ways, including in the production of polyclonal or monoclonal antibodies, in therapy (e.g., to block binding of infectious agents to alveolar cells), etc.

IMMUNOISOLATION OF TYPE I AND TYPE II ALVEOLAR CELLS

The MAbs of the invention can be used to facilitate identification and isolation of the type I or type II alveolar cells for which they are specific according to antibody-based cell separation methods that are well known in the art. Procedures for cell separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide, LDS). Red blood cells may be removed by elutriation, hemolysis, Ficoll-Paque gradients, etc. Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens. Fluorochromes which find use in a multi-color analysis include phycobiliproteins, e.g. phycoerythrin and allophycocyanins; fluorescein and Texas red.

In one embodiment of the subject invention the anti-type I cell or anti-type II cell MAb is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sulfhydryl groups and heterofunctional cross-linking reagents. A large number of heterofunctional compounds are available for linking to entities. A preferred linking group is 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, anti-type I cell or anti-type II cell MAb is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

Pure populations of type I and type II alveolar cells isolated using the MAbs of the invention can be used, for example, in the preparation of libraries for the identification of other alveolar cell-specific markers, in the preparation of implants into diseased or otherwise compromised lung tissue, and in other applications that will be readily appreciated by the ordinarily skilled artisan upon reading the present specification.

ATCC DEPOSITS

The following cell lines have been deposited on Apr. 22, 1998 with the American Type Culture Collection, 10801 University Boulevard, Manassas, Va. 20110-2209

| Deposit | ATCC Accession No. |
| --- | --- |
| Hybridoma producing anti-HTI56 monoclonal antibody | HB-12519 |
| Hybridoma producing anti-HTII280 monoclonal antibody | HB-12520 |

The invention will now be described in further detail.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1

Isolation of Type I Alveolar Cells

In order to purify type I cells, it was first necessary to establish a protocol for identifying human type I cells by techniques less time-consuming than transmission electron microscopy. The ability to identify type I cells in cytocentrifuged preparations was learned by comparing images of type I cells taken by transmission electron microscopic and thick plastic sections at the light microscopic level with cytocentrifuged preparations.

Tissue for light and electron microscopy was fixed for 2 h at room temperature in a solution of 2% glutaraldehyde, 1% freshly-prepared paraformaldehyde in 0.1 M phosphate buffer, pH 7.4, and was then postfixed overnight in 1.5% osmium tetroxide in veronal acetate buffer, pH at 4° C. Tissue was stained en bloc in 1.5% uranyl acetate in maleate buffer and was then quickly dehydrated in cold acetone and propylene oxide. The tissue was infiltrated and embedded in LX 112 (Ladd Research Industries, Burlington, Vt.). Semi-thin sections (~0.5 $\mu$m) were stained with toluidine blue and examined with a Leitz Orthoplan microscope; ultrathin sections were stained with 5% uranyl acetate and 0.8% lead citrate and then examined in a Zeiss 10 transmission electron microscope. After considerable cross-comparison of images, we were able to identify type I cells on cytocentrifuged preparations.

Human lung tissue removed during lobectomy or pneumonectomy were used; the protocol was approved by the Human Use Committee at the University of California San Francisco. A distal airway was identified, cannulated, and the cannula sutured securely into place. The lungs were lavaged six times with $Ca^{++}Mg^{++}$-free phosphate-buffered saline (PBS) containing 5 mM EDTA and 5 mM EGTA at 37° C., and then instilled with RPMI (Cell Culture Facility, UCSF) containing 10% dextran and 80 U/ml elastase (Worthington, Freehold, N.J.). The use of dextran in this and in all subsequent solutions was important for the preservation of type I cell integrity. The enzyme-instilled lungs were incubated at 37° C. for a total of 1 hour; additional elastase solution was instilled continuously to keep the lung segment inflated. Lungs were minced to 1 cu. mm. fragments, shaken in a reciprocating water bath for 5 min, and then filtered sequentially through gauze (2 ply, 1 ply) and 150$\mu$ nylon mesh (Tekto, Elmsford, N.Y.). The resultant cell suspension was separated on a discontinuous Percoll gradient (densities 1.020; 1.030; 1.035 and 1.040). By analyzing cells obtained from gradient fractions by cytocentrifuged preparations, it was found that the interface between densities of 1.035/1.040 contained the highest purity of type II cells (>50%).

Example 2

Production of Type I Cell-specific MAb

Approximately $10^7$ isolated human type I cells (described in Example 1) were centrifuged, and the cell pellet resuspended in Freund's adjuvant and used to immunize BALB/c mice. Mice were boosted with cells on days 14, 42, and 120. Spleens were removed on day 123, splenocytes were isolated and fused to NS-1 myeloma cells by conventional methods to produce hybridomas.

Seven separate fusions prepared from the spleen of immunized mice yielded approximately 5000 clones. The supernatants of these clones were screened by indirect immunofluorescence on cytocentrifuged preparations of isolated cells to select candidate clones for production of anti-against type I cell antibody. Cytocentrifuged preparations of isolated cells were prepared using a 96-well cytocentrifuge technique in order to facilitate rapid screening of the hybridomas. Glass slides (3"x4") were pre-coated with a solution of 1 mg/ml fibronectin in order to increase adherence of the cells. The slides were secured to the upper plate of a 96-well plexiglass manifold. Cells were diluted to a final concentration of 0.5 million cells/ml; 0.1 ml of the cell suspension were placed into each well and the entire apparatus was centrifuged in an IEC centrifuge at 200 rpm at room temperature for 10 minutes. Following this, the cytocentrifuged cells were allowed to partially air dry and then were placed in 1% paraformaldehyde in 0.1 M phosphate buffer (pH 7.4). Cytocentrifuged samples could be stored at 4° C. for up to two weeks prior to use.

For screening hybridoma clones, 50 $\mu$l of supernatant liquids were placed on each dot of cytocentrifuged cells, washed and secondary antibody conjugated to fluorescein was used to identify potential candidate hybridomas. Promising clones were recloned three times to homogeneity, using the same screening methodology. Finally, hybridoma supernatants were tested with 2$\mu$ thick cryostat sections of human lung in order to further verify that the supernatant was reactive only against type I cells. Many clones were discarded because supernatants exhibited cross-reactivity with other cell types in addition to type I cells. Promising clones were subcloned three times.

The use of cytospin preparations in the rapid screening format proved to be very important in the identification of an anti-type I cell MAb. Screening of the hybridoma supernatants using thin sections of lung tissue was not possible for at least four reasons. First, mixed cell preparations were used for screening antibodies, allowing for the identification and discarding of antibodies that cross-reacted with airway cells or other cell types. Second, the ability to process 96 samples simultaneously allowed for screening of sufficient numbers of monoclonals to identify the one positive clone; this would not have been possible using sections of lung tissue. The long turnaround time in cutting cryostat sections thin enough (1–2 $\mu$m) to recognize the apical portion of type I cells and the inability to use a multiple-well format precluded effective screening of candidate clones. Third, cryostat sections are small and most do not contain airways or vasculature, so that clones reacting with multiple cell types would not be recognized. Fourth, screening on lung tissue stored in paraffin would have not been fruitful because fixation and embedding in paraffin destroys the antigenicity of many proteins, so that the tissue does not react with monoclonal antibodies. Indeed, it was later discovered that the anti-type I cell MAb described herein does not react with conventionally-fixed paraffin-embedded tissue, so that HTI56 would not have been recognized had we used paraffin-embedded tissue for screening.

As a result of seven fusions and screening of approximately 5000 clones, a total of four promising monoclonal antibodies were produced. Two of these antibodies, one of the $IgG_1$ subclass and the other of the $IgG_{2a}$ subclass are by Western blotting specific for a lung protein of apparent MW 56 kDa. The $IgG_1$ antibody was selected for more detailed analysis because it appeared to give the strongest signal by immunofluorescence.

Characterization of Anti-type I Alveolar Cell MAb: Binding to Human Lung Tissue

The specificity of the anti-type I cell MAb for type I alveolar cells was examined using immunofluorescent antibody staining of human lung tissue. Human lung tissue was fixed in a solution of freshly prepared 4% paraformaldehyde in 0.1 M phosphate buffer, pH 7.4, cryoprotected by overnight submersion in 30% sucrose at 4° C., then transferred to O.C.T. (Tissue Tek), and frozen in Freon 22 and liquid nitrogen. Cryosections (2 $\mu$m) were picked up on Superfrost Plus slides (Fisher Scientific Co.) and rings of rubber cement were applied around the sections to form wells to contain solutions. Tissue was sequentially immersed in the following solutions: 0.1% BSA/PBS plus 0.3% triton (BPT); 10% normal goat serum in BPT; primary MAb in BPT overnight at 4° C.; BPT; goat anti-mouse IgG conjugated to FITC or rhodamine (affinity purified, from Organon Teknika Cappel, Durham, N.C.) in BPT. Sections were briefly rinsed in distilled water, rubber cement wells were removed, tissue was briefly dried, and cover slips were mounted with DABCO (2.5% 1,4-diazobicyclo-2,2,2-octane, 10% PBS in glycerin, pH 8.6). The anti-HTI56 MAb specifically bound type I alveolar cells in human lung tissue samples. All type II alveolar cells, airway cells, interstitial cells, blood vessels, and macrophages were negative for immunofluorescence staining using the isolated anti-HTI56 MAb.

Characterization of Anti-type I Alveolar Cell MAb: Binding to Tissues of Other Organs The binding of the anti-HTI56 MAb was also examined in homogenated tissue from human brain, skin, trachea, lung, esophagus, stomach, intestine, urinary bladder, blood, kidney, spleen, and liver, as well as rat lung and mouse lung tissues. Tissue from each organ was frozen at −70° C., pulverized in a mortar and pestle, and then extracted in 150 mM NaCl, 0.2 mM EDTA, 0.5 mM PMSF, 5 mM iodoacetamine, 50 µg DNAse and 4% SDS for two hours. After centrifugation at 150×g, the supernatant liquid was removed. Samples from each organ tissue were analyzed by Western blot using the MAb and performed according to conventional methods using non-reducing SDS-PAGE (10% acrylamide, 4% stacking gel; 0.1% SDS) (it was later found that antigenicity of the HTI56 polypeptide is lost if SDS-PAGE is performed under reducing conditions).

The MAb bound a polypeptide of approximately 55 to 56 kDa in the sample of lung homogenate. The human lung polypeptide bound by the MAb was termed HTI56; likewise, the MAb identified in this example is termed anti-HTI56 MAb. While the anti-HTI56 MAb bound to human lung tissue by Western blot, no binding was detected in any of the other human tissues tested or in the samples from rat lung or mouse lung. These results were further confirmed by immunocytochemistry.

Characterization of Anti-type I Alveolar Cell MAb: EM Immunocytochemistry

Ultrathin cryosections of human lung tissue were cut at −100° C. from tissue blocks fixed in 4% paraformaldehyde in 0.1 M cacodylate buffer, pH 7.4, cryoprotected by overnight submersion in 2.3 M sucrose in phosphate buffer, and frozen in Freon 22 and liquid nitrogen. Ultrathin sections were picked up on droplets of sucrose, transferred to grids, and collected on agarose-gelatine plates. The immunocytochemistry reactions followed the same initial sequence as above but with the omission of triton; the grids were floated face down on drops of solution on dental wax. The secondary antibodies for transmission electron microscopy visualization were conjugated to 5 nm colloidal gold (Aurion ImmunoGold, Electron Microscopy Services, Fort Washington, Pa.). After secondary antibody incubation, the grids were rinsed in distilled water, stained with 2% uranyl acetate/0.15 M oxalate, pH 7.0, and "embedded" in a thin layer of 0.2% aqueous uranyl acetate/2% methyl cellulose.

The apical plasma membrane was immunoreactive, while cytoplasm and basolateral membranes were not decorated with immunogold. These data show that HTI56 is present on the apical surface of type I alveolar cells.

Example 3

Purification of the Type I Cell-specific Polypeptide HTI56

One hundred grams of distal human lung tissue was minced to 1 cu. mm fragments and diluted with 400 ml of Solution A (250 mM sucrose, 150 mM ammonia sulfate, pH 7.4), containing buffer S (2 mM EDTA, 2 mM EGTA, 50 µg/ml DNAase, 50 µg/ml RNAase, 0.5 mM PMSF and 5 mM iodoacetamide) at 4° C. The lung fragments were then homogenized with a Polytron (Brinkman) tissue homogenizer at setting 6 for 1 min. The homogenate was diluted to 600 ml with Solution A and homogenized again for one minute. The homogenate was stirred for 10 min and centrifuged at 400×g for 15 min. at 4° C. The supernatant was resuspended in Solution A and pelleted at 100,000×g for 2 hrs at 4° C. Pellets were dissolved in extraction buffer (9.5 M urea, 5% MEGA-8, 2% ampholines, 5% glycerol) for 2 hours at room temperature.

The extract was centrifuged at 100,000×g for 2 hours at 4° C., and the clear supernatant liquid was loaded onto a preparative isoelectric focusing column (Rotofor, Biorad). The column was run at 13W constant power until the voltage stabilized. Fractions containing partially purified antigen were pooled and NaCl was added to a final concentration of 2.0 M. The protein was then dialyzed extensively against 500 mM NaCl, 50 mM Tris-B, pH 7.2 containing 1% MEGA-8. The dialyzed protein was passed through a cross-linked dextran column (Sepharos, Pharmacia) and then added to a WGA column. HTI56 bound to the immobilized lectin was washed with buffer containing 0.1 M NaCl and then eluted from the column using buffer containing 0.2 M N-acetyl-glucosamine. HTI56 containing fractions eluted from the column was dialyzed overnight against 2% SDS, 10% glycerol and 50 mM Tris -base, pH 6.8. The sample was concentrated and then separated by 2-dimensional electrophoresis. HTI56 was purified to homogeneity as determined by 2-dimensional Western blot analysis.

Example 4

Alternative Method of Purification of the Type I Cell-specific Polypeptide HTI56

The clear supernatant liquid from the second ultracentrifugation described above in Example 3 was loaded onto a Sepharose Q column (Pharmacia) pre-equilibrated with extraction buffer. The column was washed with a discontinuous gradient of KCl (0.05 M and 0.20 M) in extraction buffer. Bound HTI56 was eluted with 0.20 M KCl and dialyzed extensively against 5 mM Tris-base, pH 8.0, containing 2 mM EDTA and 2 mM EGTA. HTI56 was purified further by reverse phase HPLC on a C4 column (Vydac) pre-equilibrated with formic acid/water (3:2, v/v) (buffer A) and eluted with a 30 min. linear gradient of formic acid/acetonitrile (3:2, v/v) (Solution B). Eluted fractions containing HTI56 were concentrated and then purified by reverse phase HPLC on a cross linked Sepharose column (Pharmacia, Superose) and eluted with a 30 minute linear gradient of Solutions A and B. Fractions from the Superose column containing purified protein were pooled and lyophilized. Purified material was applied to a C8 column (Vydac) using a 30 min. linear gradient and buffers A and B.

Example 5

Characterization of HTI56

Purified HTI56 was found to be N-terminus blocked, since CNBr cleavage of the purified protein did not yield sufficient quantities of peptides to obtain internal sequence. The purified protein has a pi of 4.3–5.6 (mean 4.95). HTI56 is poorly soluble in aqueous medium, an dis not readily solublized by high salt concentration. HTI56 can be solublized in urea and guanidine hydrochloride. Treatment with glycosidases lowers the apparent MW of HTI56, but not its antigenicity. Two-dimensional gel electrophoresis indicates that HTI56 has an approximately 1 pH unit charge train. These latter two observations indicate that HTI56 is glycosylated. Analysis of human fetal tissue showed that HTI56 is detectable by immunocytochemistry in occasional potential airspace at approximately weeks 18 and 20 of gestation. Culture of fetal lung explant tissue for four days induces expression of HTI56 diffusely in cells lining potential airways.

In marked contrast to the 55 kDa protein described by Singh et al. ((1993) *Microscopy Res. Tech.* 26:357–65), which is found in many other cell types and in organs other than lung and has a pI with a single sharp band at 4.3, HTI56 has a more alkaline pI and a large charge train, suggesting that HTI56 is posttranslationally modified. The binding of HTI56 to a column of immobilized wheat-germ agglutinin provides further evidence of its posttranslational modification, suggesting that HTI56 contains sialic acid and/or β-D-N-acetyl-glucosamine residues.

Example 6
Detection of Lung Injury Using Anti-type I Cell-specific MAb in Pulmonary Edema Fluid Samples
a) Samples and Patient Population Edema fluid samples (and, simultaneously, plasma samples) were obtained from patients in the intensive care unit at Moffitt Hospital, University of California (UCSF) Medical Center. The patients from whom samples were taken had undergone endotracheal intubation for acute respiratory failure. Samples were collected according to the study protocol approved by the Committee on Human Research at UCSF. All of the patients had clinical and radiological evidence of pulmonary edema.

The samples were collected as soon as possible following endotracheal intubation from patients with evidence of pulmonary edema, as described previously (Sprung et al. (1981) *Am. Rev. Respir. Dis.* 124:718–22). Briefly, a 14 gauge silastic catheter was inserted through the endotracheal tube and advanced into a wedged position in the distal airspaces. Gentle suction was applied as the catheter was withdrawn and the edema fluid was collected in a suction trap. In some cases it was necessary to make repeated passes to obtain an adequate volume of at least 5 mls. There was no saline instillation prior to suctioning. Edema fluid samples were collected within 15 min of endotracheal intubation or as soon as there was evidence of pulmonary edema in those patients that were already intubated (e.g. patients electively intubated for surgery). Samples were centrifuged at 3000×g for 10 min and the supernatant liquid was frozen at −70° C. until the samples were processed. Simultaneous blood samples were obtained from each patient at the time of edema fluid sampling. The blood was collected in citrated buffer, centrifuged at 3000×g for 10 min, and the plasma was removed and stored at −70° C.

Samples were selected for this study according to clinical criteria from a group of samples collected between January 1996 and May 1997. For the purpose of this study, two distinct patient groups were characterized; patients with acute lung injury and those with pulmonary edema from presumed hydrostatic causes. Patients were grouped according to edema fluid protein/plasma protein ratios. Patients were classified as "acute lung injury" if the ratio was greater than 0.75 and as "hydrostatic pulmonary edema" if the ratio was less than 0.65, as described previously (22–25). Patients were excluded from this study if the protein ratio was intermediate (between 0.65–0.75), if there were clinical circumstances that might confuse the interpretation of the results (e.g., alveolar proteinosis), or if there was an inadequate amount of sample to assay. The assays were performed blinded as to the two groups.

b) Preparation of Test and Control Samples

Each edema fluid was assayed for total protein content using the bicinchoninic method (Smith et al. (1985) *Anal. Biochem.* 150:76–85), BCA Protein Assay (Pierce Corp., Rockford, Ill.). Because purified HTI56 polypeptide was not yet available in sufficient quantity to use as a standard, human lung homogenate (HLH) was prepared for use in a standard curve for each assay of HTI56. HLH was prepared from a portion of grossly normal appearing lung tissue obtained intraoperatively from a patient undergoing a lobectomy for a pulmonary tumor. The tissue was chopped into 1–2 cm$^3$ pieces, frozen in liquid nitrogen, and stored at −70° C. The tissue was thawed, minced to 1 mm$^3$ fragments and incubated for 30 min at 27° C. in a solution of 5 mM Tris, pH 8.0, 0.1% octanoyl-N-methylglucamide (MEGA-8, Calbiochem, LaJolla, Calif.), 2 mM EDTA, 2 mM ethylene glycol-bis (B-aminoethyl ether) N,N,N',N'-tetra acetic acid (EGTA), 5 mM iodoacetamide and 0.5 mM phenyl-methyl-sulfonyl fluoride (PMSF). The lung pieces were homogenized with a Brinkman Polytron at setting "6" for 30 seconds and centrifuged at 1000×g for 20 min. The supernatant liquid was centrifuged at 100,000×g for 1 hr at 4° C. and the pellet was dissolved by gentle agitation in a solution of 9.5 M urea, 4% MEGA-8, 10 mM KOH, 2 mM EDTA, 2 mM EGTA, 5 mM iodoacetamide and 5 mM PMSF, pH 6.8 for 2 hrs at 22° C. The extract was centrifuged at 20,000×g for 30 min, the supernatant was gently removed and centrifuged at 200,000×g for 2.5 hrs, and the pellet was discarded. The final extracted and solublized lung homogenate was divided into 500 10 µl aliquots and stored at −70° C.

c) Quantitation of HTI56 by Dot Blotting

Serial dilutions of each sample were assayed with concomitant HLH standard curves to determine the amount of HTI56 in each sample relative to that found in the homogenate. Results are expressed as HTI56 in arbitrary units of HLH.

HLH was diluted in a solution of 50 mM NaHCO$_3$ (pH 9.4), 2 M urea, 0.2% MEGA-8 and 2 mg bovine serum albumin/ml. Edema fluid samples were first diluted 1:10 in sterile water and then into 2 M urea, 0.2% MEGA-8, 50 mM NaHCO3 (pH 9.4). Serial dilutions of HLH and serial dilutions of edema fluid samples were dot blotted in duplicate on the same piece of nitrocellulose. The final protein concentration was adjusted to 2 mg/ml by the addition of bovine serum albumin and to 200 µl final volume.

Nitrocellulose blots of edema fluid samples were processed by first quenching endogenous peroxidase activity by incubating the blots in 15% hydrogen peroxide in water for 20 min. Non-specific binding was blocked by a 2 hr incubation of the membrane in a solution containing 1% non-fat dried milk, 0.4% fish gelatin, 0.1% bovine serum albumin (BSA), 0.9% NaCl, 10 mM Tris-Base (pH 7.2) and 1.5% sheep serum (Sigma, St. Louis, Mo.). The blots were then incubated for 18 min with purified anti-HTI56 MAb (1:500 solution of antibody in 20 mM Tris-buffered saline, pH 7.4 (TBS-T)), washed 20 times with TBS-T during 1 hour, incubated for 18 min in a 1:10,000 dilution in TBS-T of HRP-labeled, affinity-purified, sheep anti-mouse IgG (Cappel, ICN Pharmaceuticals, Aurora, Ohio), and then washed with TBS-T 20 times over 1 hour. The blots were treated with a solution containing luminlol (ECL Light Detection System, Amersham) for 1 min. Bound secondary antibody was quantified in a plate luminometer (Packard Instrument Co., Downers Grove, Ill.); some but not all dot blots were also visualized by brief exposure to autoradiography film (Amersham, Arlington Heights, Ill.).

HTI56 content was determined by comparing units of emitted light in serial dilutions of edema samples to that of serial dilutions of human lung homogenate on the same piece of nitrocellulose. Duplicate numerical values for each dilution of sample and standard were averaged. Background (determined by averaging the values of all the empty wells) was subtracted from each sample. Nonspecific signal, obtained from the sample processed as above but without primary antibody, was measured for each sample and subtracted from the final value. From the serial dilutions of HLH, a standard curve with linear regression was created (FIG. 1) (Statview, Abacus Concepts, Berkeley, Calif.). HTI56 is expressed as an arbitrary unit based on the equivalent HTI56 content of the HLH standard (expressed in $\mu$g protein).

To control for the any effects of the variable total protein/sample, all samples were adjusted to the same total protein content by the addition of BSA. $HTI_{56}$ was solublized and binding to nitrocellulose was optimized by the addition of previously-determined detergent-containing buffers to each sample. All samples and standards were standardized to 200 $\mu$l volume.

To determine the potential inhibitory or enhancing effects of unknown substances in the samples on the measurement of HTI56, "spiking" experiments were performed on samples in which there was sufficient quantity. Specified amounts of standard were combined with the samples and also dot blotted separately. Measured HTI56 agreed within 10% to values calculated by adding separately-assayed samples and standards.

As a control for variability among assays, fresh aliquots of the same HLH were used to generate standard curves for each assay; when quantity of sample permitted, samples were run with several different standard curves to establish that the results were not variable.

As evidenced by the results presented below, the light-based ELISA for $HTI_{56}$ was highly sensitive, requiring only 0.5–10 $\mu$l of pulmonary edema fluid (and 30–50 $\mu$l of plasma, as discussed in Example 8 below). The sensitivity of the assay permitted accurate measurements over a wide range of unknown quantities of $HTI_{56}$ in the samples. The standard curve was linear over a 10–15 fold range. The correlation coefficient (r) values for the standard curves ranged between 0.98 and 0.99 (FIG. 1).

Data is presented as mean +/− standard deviation. Comparison between groups was performed using the Mann-Whitney U test for nonparametric consideration of the two-tailed null hypothesis (28). Statistical significance was defined as p<0.05.

d) Results

Table 1 summarizes the clinical diagnosis, outcome, and edema fluid/plasma protein ratios for the 15 patients included in the acute lung injury group. Although all of the patients in this group had severe respiratory failure and pulmonary edema, the patients were clinically heterogeneous. All of the "acute lung injury" patients had clinical circumstances compatible with an increased permeability mechanism of pulmonary edema; $HTI_{56}$ was assayed in the edema fluid of all 15 of these patients. The average edema fluid/plasma protein ratio for the acute lung injury group was 1.04+/−0.2. Survival in this group was 40% (6/15).

TABLE 1

Clinical characteristics of patients with acute lung injury

| Pt No. | Edema Fluid/Plasma Protein Ratio | Age | Sex | Primary Clinical Disorder | Outcome |
|---|---|---|---|---|---|
| 1 | 1.25 | 20 | F | Aspiration pneumonia | Survived |
| 2 | 1.13 | 20 | M | Sepsis/pneumonia | Expired |
| 3 | 0.88 | 21 | M | Pneumonia | Expired |
| 4 | 1.31 | 48 | M | Fungal sepsis | Expired |
| 5 | 1.13 | 48 | M | Sepsis | Expired |
| 6 | 1.12 | 69 | M | Pneumonia | Expired |
| 7 | 0.96 | 21 | M | Overdose/aspiration pneumonia | Expired |
| 8 | .75 | 40 | F | Sepsis | Survived |
| 9 | 1.47 | 29 | F | Septic abortion | Survived |
| 10 | 0.88 | 38 | M | Sepsis | Survived |
| 11 | 0.85 | 81 | M | Pneumonia | Expired |
| 12 | 1.07 | 32 | F | Overdose/aspiration pneumonia | Survived |
| 13 | 0.80 | 25 | F | Overdose/aspiration pneumonia | Expired |
| 14 | 1.17 | 62 | M | Aspiration pneumonia | Expired |
| 15 | 0.93 | 67 | M | Pneumonia | Survived |

The clinical characteristics of the 12 patients in the hydrostatic pulmonary edema group is summarized in Table 2. All of the patients in this group had clinical findings compatible with a hydrostatic mechanism of pulmonary edema. The average edema fluid/plasma protein ratio was 0.43+/−0.1; survival was 83% (10/12).

TABLE 2

Clinical characteristics of patients with hydrostatic pulmonary edema

| Pt No. | Edema Fluid/Plasma Protein Ratio | Age | Sex | Primary Clinical Disorder | Outcome |
|---|---|---|---|---|---|
| 1 | 0.65 | 77 | F | Acute MI | Survived |
| 2 | 0.42 | 65 | F | Fluid overload | Survived |
| 3 | 0.52 | 33 | M | Hepatic insufficiency/CHF | Expired |
| 4 | 0.33 | 54 | M | Drug toxicity/CHF | Expired |
| 5 | 0.52 | 49 | M | Fluid overload/CHF | Survived |
| 6 | 0.29 | 52 | F | Recurrent CHF | Survived |
| 7 | 0.27 | 63 | M | Recurrent CHF | Survived |
| 8 | 0.46 | 80 | M | Recurrent CHF | Survived |
| 9 | 0.42 | 68 | M | Recurrent CHF | Survived |
| 10 | 0.44 | 25 | M | Fluid overload | Survived |
| 11 | 0.39 | 52 | M | Acute MI | Survived |
| 12 | 0.52 | 76 | M | Acute MI | Survived |

MI = myocardial infarction; CHF = chronic heart failure

Because of the finite protein binding capacity of nitrocellulose and the relatively high concentration of protein in some of the samples, we tested the effects on the assay of total protein in the sample. Neither the sensitivity nor the accuracy of the measurement of HTI56 was affected by total protein concentrations less than or equal to 10 mg/ml. The sensitivity of the assay decreases gradually between about 10 to 15 mg of protein/ml. At concentrations greater than 15 mg/ml, sensitivity was significantly decreased. All samples, diluted as necessary for the assay, contained far less (<1 mg/ml) than this amount of total protein. In order to ensure uniformity, the protein of each sample was adjusted to 2 mg/ml by the addition of serum albumin.

Figure 2:
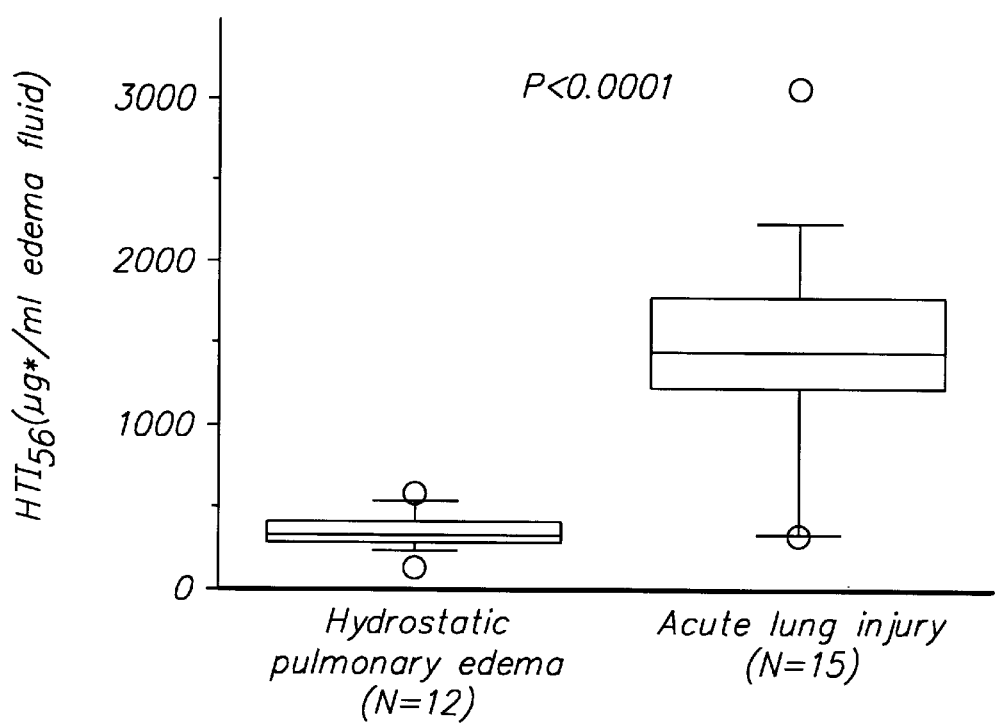
FIG. 2 is a box plot of HTI56 content of edema fluid samples.

Pulmonary edema fluid HTI56 from the two clinical groups are shown in Table 3 and summarized in FIG. 2. The average quantity of HTI56 was about 4.3-fold greater in the lung injury group than the hydrostatic group, with p<0.0001. Also, we found that the airspace content of protein and HTI56 varied independently.

TABLE 3

HTI56 content of lung edema fluid

| Acute Lung Injury | | Hydrostatic Pulmonary Edema | |
|---|---|---|---|
| Pt. No. | HTI56 Content ($\mu$g*/ml edema fluid) | Pt. No. | HTI56 Content ($\mu$g*/ml edema fluid) |
| 1 | 1631 | 1 | 270 |
| 2 | 1227 | 2 | 1123 |
| 3 | 1203 | 3 | 348 |
| 4 | 286 | 4 | 584 |
| 5 | 1786 | 5 | 500 |
| 6 | 1480 | 6 | 302 |
| 7 | 299 | 7 | 403 |
| 8 | 1414 | 8 | 310 |
| 9 | 2013 | 9 | 399 |
| 10 | 1328 | 10 | 277 |
| 11 | 3025 | 11 | 251 |
| 12 | 1414 | 12 | 253 |
| 13 | 1259 | | |
| 14 | 1188 | | |
| 15 | 2207 | | |
| Average | 1451 ± 727 | Average | 335 ± 123 |

*$\mu$g of HLH containing equivalent amount of HTI56

All sample and standard $HTI_{56}$ quantities were corrected by subtraction of "nonspecific signal" (i.e. signal from a sample without primary antibody) as outlined previously. The standard consistently had less than 2% nonspecific signal. Out of 27 total edema fluid samples, 26 had less than 6% nonspecific binding. One sample in the lung injury group (patient #7) exhibited a much higher non-specific signal, ~25%. Although we do not know the cause of this nonspecific binding, this sample appeared to contain more hemolyzed blood than did the other samples. Interestingly, this sample was one of two acute lung injury samples (the other being patient #4) that contained much less $HTI_{56}$ than the others.

"Spiking experiments" performed with random edema fluid samples showed no effect on antigen quantification in the standard by potential interfering substances in the samples. Sample #7 was not tested in this way because of insufficient quantity.

These data show that the amount of $HTI_{56}$ in pulmonary edema fluid is significantly greater in patients with acute lung injury than it is in a control group of patients. HTI56 was elevated approximately 4.5 fold in edema fluid from the acute lung injury group relative to the control group with hydrostatic pulmonary edema. All of the patients with hydrostatic pulmonary edema had low edema fluid HTI56 values; there was little variability. Eighty seven percent (13/15) of the patients with acute lung injury had HTI56 edema fluid contents 2–5× that of the highest level found in the control group.

The lower HTI56 values in two patients whose clinical data were compatible with the diagnosis of acute lung injury could not be fully explained, although the edema fluid from one of these two patients had an unusually high amount of nonspecific binding. Without being held to theory, one possible explanation for the lower HTI56 values in these two patients may have to do with the relationship between the time course of lung injury and the presence of HTI56 in the alveolar space. For example, although the edema fluid was obtained from all patients as soon after intubation as possible, acute injury may have occurred at various intervals prior to intubation. Since HTI56 may not remain within the alveolar space for extended periods of time, the relative amount of HTI56 in edema fluid samples may provide clues as to the time of an earlier lung injury. In addition, since different pathogenic mechanisms of lung injury may differ with the clearance time of HTI56 from the alveolar space, HTI56 may also be a useful marker in determining the timing of lung injury and provide clues as to the causative mechanism. For example, HTI56 may be particularly useful in these determinations when combined with other available assays and information about the patient's condition. Furthermore, the level of HTI56 marker may be assayed in serial samples with time, e.g, as is the common practice for measurement of cardiac isoenzymes (e.g., CPK, LDH) in myocardial infarction, in which the time course of both increase and decrease of the cardiac marker varies with the marker selected.

We found that the ratio of edema fluid protein to HTI56 was variable, similar to the findings of $RTI_{40}$ in rodent models of lung injury in which the airspace contents of protein and RTI40 varied independently (McElroy et al. (1995) *Am. J. Physiol: Lung Mol. Biol.* 12:L181–6). This supports the notion that, in contrast to protein, HTI56 in the alveolar space originates from one source, the type I epithelial cells. This specificity makes HTI56 potentially a more valuable marker than gross protein levels, which may be derived from multiple sources and may be cleared by many different mechanisms.

Example 7

Detection of Lung Injury Using Anti-type I Cell-specific MAb in Plasma Samples

Plasma samples obtained from the patients described in Example 6 above. Control plasma obtained from 11 healthy volunteers with no known history of cardiac or pulmonary disease were analyzed.

Blots of plasma samples were processed somewhat differently than those of edema fluid samples as described in Example 7 in order to minimize the greater amount of nonspecific binding of the secondary antibody to plasma components. The plasma blots were treated with 15% hydrogen peroxide for 30 min, washed 4 times with sterile water, and incubated for 2 hrs in a solution containing 1% nonfat dried milk, 0.4% fish gelatin, 0.1% bovine serum albumin, 0.9% NaCl, and 10 mM Tris base, pH 7.2. Blots were incubated for 20 min with a 1:1000 dilution of biotinylated primary antibody (prepared by the succinimide ester method (Bayer et al. (1980) *Methods Biochem. Anal.* 26:1–45)) in TBS-T. Following incubation with the biotinylated primary antibody, the blots were washed 20 times with TBS-T over one hour, incubated with a 1:10,000 dilution of HRP-streptavidin (Sigma, St Louis, Mo.), and finally washed again 20 times with TBS-T over 1 hour. Bound antibody was quantified after exposure to Luminlol, as previously described.

Quantification of HTI56 in Plasma

Figure 3:
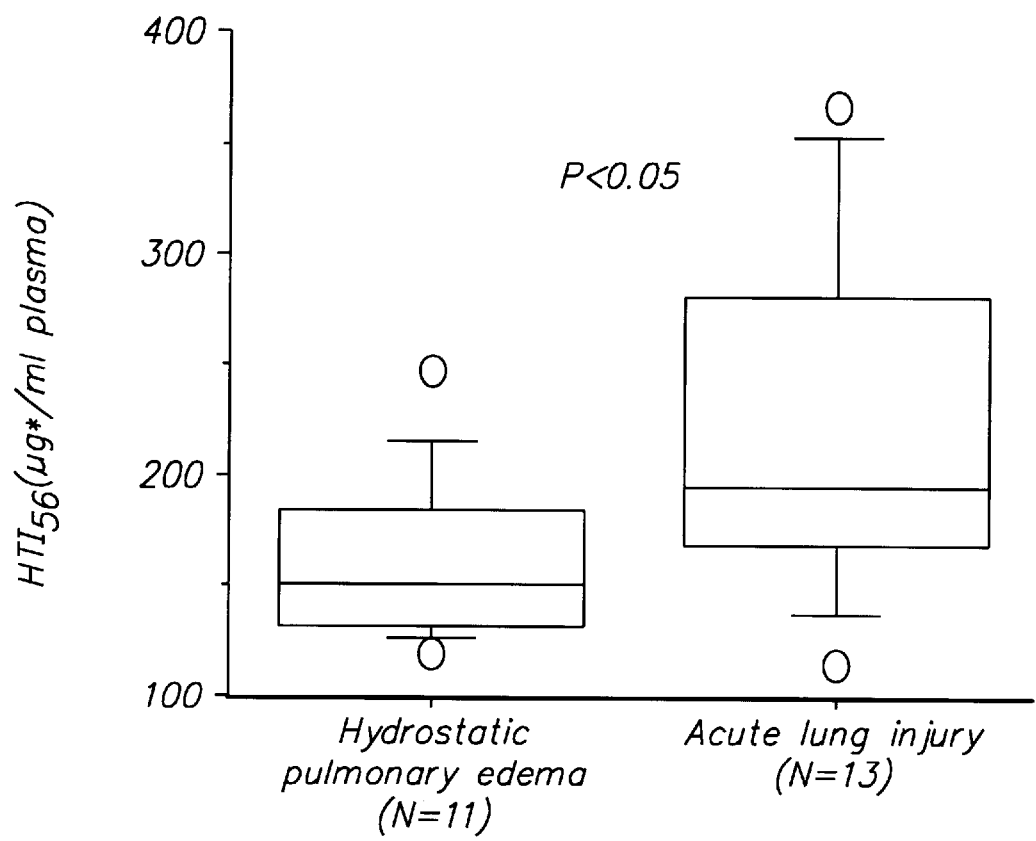
FIG. 3 is a box plot of HTI56 content of plasma samples.

Plasma from 13 of the acute lung injury patients, 11 of the hydrostatic patients (3 patient plasma samples were not available), and 11 normal volunteers were assayed for HTI56 (Table 4). The plasma content of HTI56 was significantly greater (1.4×) in the acute lung injury group than that in the hydrostatic group, p<0.05 (FIG. 3). Plasma of 11 normal volunteers contained low levels of antigen with little variability.

TABLE 4

HTI56 content of lung edema fluid

| Acute Lung Injury | | Hydrostatic Pulmonary Edema | | Normal | |
|---|---|---|---|---|---|
| Pt. No. | HTI56 Content (μg*/ml plasma) | Pt. No. | HTI56 Content (μg*/ml plasma) | Pt. No. | HTI56 Content (μg*/ml plasma) |
| 1 | 200 | 1 | 136 | 1 | 155 |
| 2 | 305 | 2 | 247 | 2 | 112 |
| 3 | 169 | 3 | 149 | 3 | 119 |
| 4 | NA | 4 | 119 | 4 | 143 |
| 5 | 149 | 5 | 170 | 5 | 134 |
| 6 | NA | 6 | 188 | 6 | 154 |
| 7 | 192 | 7 | 192 | 7 | 130 |
| 8 | 366 | 8 | 145 | 8 | 137 |
| 9 | 227 | 9 | NA | 9 | 151 |
| 10 | 164 | 10 | 128 | 10 | 127 |
| 11 | 342 | 11 | 128 | 11 | 140 |
| 12 | 200 | 12 | 160 | | |
| 13 | NA | | | | |
| 14 | 172 | | | | |
| 15 | 113 | | | | |
| Average | 217 ± 79 | Average | 160 ± 38 | Average | 137 ± 14 |

*μg of HLH containing equivalent amount of HTI56

In the 35 samples of plasma, 27 samples had less than 1% nonspecific binding, 34 had less than 6%, and one sample contained 15% nonspecific binding. All final plasma HTI56 values were corrected for nonspecific signal as described previously. "Spiking" experiments performed on random plasma samples yielded similar results (agreement within 10%) to similar experiments performed with edema fluid.

These data show that the amount of HTI56 in pulmonary edema fluid is significantly greater in patients with acute lung injury than it is in a control group of patients. Although the mechanism for this observation is unknown, there may be a disruption in the air/blood barrier in acute lung injury, as has been hypothesized for the finding of surfactant-associated proteins in serum (Doyle et al. (1995) *Am. J. Respir. Crit. Care Med.* 152:307–17; Doyle (1995) *Am. J. Respir. Crit. Care Med.* 151:A73). However, it is not necessary to hypothesize direct entry from the airspace into the vasculature, because interstitial HTI56 could enter the blood stream via normal clearance via pulmonary lymphatics and the thoracic duct. Interestingly, we found a baseline, but low, level of HTI56 in the plasma of normal controls. The tissue source of HTI56 in normal plasma is unknown; we have not been able to detect HTI56 in organs other than lung by either Western blot analysis or immunocytochemical methods. The observation that the plasma content of HTI56 is elevated in acute lung injury is important, as it indicates that blood HTI56 can be used as an important marker for acute lung injury.

Example 8
Isolation of Type II Alveolar Cells

Type II cells were isolated by similar methods to those described for type I cells (Example 1), with the following changes. The concentration of elastase used was 40 U/ml. After the filtering step, cells were plated on plastic petri dishes that had been coated with a solution of human IgG (100 mg/ml) in order to remove macrophages and lymphocytes containing Fc receptors. Type II cells were identified by the modified Papanicolaou stain, a method commonly employed to identify this cell type in cytocentrifuged preparations (for review, see Dobbs, (1990) *Am. J. Physiol.: Lung Cell Mol. Physiol.*, 2:L134–L147)

Example 9
Production of Human Type II Cell-specific MAb

Immunization of mice, production of hybridomas, and screening of monoclonal antibodies specific for human type II cells were performed as described above for production of anti-type I cell MAbs. Seven fusions were performed as described for the production of the monoclonal antibodies against human type I cells. None of these produced a hybridoma specific for human type II cells.

Immunization of mice was repeated using isolated human type II cells, but using a different method. Mice were injected intradermally with about $10^7$ isolated human type II cells and boosted 7 days later by intrasplenic injection. Spleens were harvested for fusion on day 10. Hybridoma supernatants were screened as described for type I cells and one hybridoma clone that produced an IgM antibody specific for human type II cells was identified using the cytocentrifugation screening technique described above. Western blot analysis of human lung homogenate revealed that the identified IgM MAb bound a polypeptide of approximately 240–280 kDa; this polypeptide was termed HTII280. Antibody binding to HTII280 was unaffected by reduction. The MAb that binds this polypeptide was termed the anti-HTII280 MAb.

The specificity of the anti-HTII280 MAb for type II alveolar cells was examined using immunofluorescent antibody staining of human lung tissue as described above. The anti-HTII280 MAb specifically bound type II alveolar cells in human lung tissue samples. All type I alveolar cells, airway cells, interstitial cells, and blood vessels were negative for immunofluorescence staining using the isolated anti-HTI56 MAb.

The binding of the anti-HTII280 MAb was examined in tissue homogenates of human brain, skin, trachea, lung, esophagus, stomach, intestine, urinary bladder, blood, kidney, spleen, and liver by Western blot performed according to conventional methods using reducing SDS-PAGE (6% acrylamide, 4% stacking gel, 0.1% SDS). The anti-HTII280 MAb bound a polypeptide of approximately 240–280 kDa in the sample of lung homogenate; however, no binding was detected in any of the other human tissues tested.

Example 10
Purification of HTII280

HTII280 was partially purified from lung homogenate as described above in the second method for purification of HTI56 to the point of loading the sample on the Sepharose Q column. The columns was washed with 0.20 M KCl and HTII280 was eluted with 0.30 M KCl in extraction buffer.

Example 11
Detection of Lung Injury Using Anti-type II Cell MAb

In a preliminary experiment, samples were obtained from test patients (acute lung injury associated with adult respiratory distress syndrome) and normal patients (intubated patients with non-pulmonary pathology) performed by bronchoalveolar lavage (BAL) by conventional techniques. The samples were assayed as described in Example 6 above, except that the anti-HTII280 MAb was substituted for the anti-HTI56 MAb. The data appear in Table 5.

TABLE 5

Measurement of HTII280 in lavage samples

| Sample ID | Total Protein | HTII280 per ml* |
|---|---|---|
| Normals | | |
| DP9548 | 108 | 139 |
| DP9654 | 99.3 | 83 |
| DP9712 | 81.3 | 29 |
| Test | | |
| ASC788 | 3563 | 182 |
| ASC49 | 1180 | 210 |
| ASC545 | 4607 | 305 |

*Arbitrary units expressed as human lung equivalent.

These preliminary data indicate HTII280 can be useful as a marker for acute lung injury.

What is claimed is:

1. A method for detecting lung injury in a human subject, the method comprising the steps of:

contacting a specific anti-human type I alveolar cell monoclonal antibody with a test sample from a subject suspected of having acute lung injury, wherein the sample is suspected of comprising a human type I alveolar cell-specific polypeptide; and detecting specific binding of the anti-human type I alveolar cell monoclonal antibody to the human type I alveolar cell-specific polypeptide in the sample;

wherein detection of specific binding of the anti-human type I alveolar cell monoclonal antibody to human type I alveolar cell-specific polypeptide in the sample at a level substantially elevated relative to a level in a normal subject is indicative of acute lung injury in the subject.

2. The method of claim 1, wherein the human type I alveolar cell-specific polypeptide is HTI56.

3. The method of claim 1, wherein the monoclonal antibody is the monoclonal antibody produced by hybridoma cell ATCC accession no. HB-12519.

4. The method of claim 1, wherein the sample is a pulmonary edema fluid sample.

5. The method of claim 1, wherein the sample is a plasma sample.

6. The method of claim 1, wherein the sample is a urine sample.

7. The method of claim 1, wherein said detecting is by:

immobilizing polypeptides in the test sample on a solid support;

contacting the immobilized polypeptides with the anti-human type I alveolar cell monoclonal antibody, wherein the antibody is detectably labeled with a label which generates a luminescent signal; and detecting specific binding of the anti-human type I alveolar cell monoclonal antibody using a luminometer.

* * * * *